United States Patent [19]

Schmidt et al.

[11] Patent Number: 4,732,991

[45] Date of Patent: Mar. 22, 1988

[54] SUBSTITUTED PHTHALIDES

[75] Inventors: Paul J. Schmidt, Sharonville; Nathan N. Crounse, Cincinnati, both of Ohio

[73] Assignee: Hilton Davis Chemical Co., Cincinnati, Ohio

[21] Appl. No.: 830,300

[22] Filed: Feb. 18, 1986

Related U.S. Application Data

[60] Division of Ser. No. 793,544, May 4, 1977, abandoned, which is a continuation-in-part of Ser. No. 726,482, Sep. 24, 1976, abandoned.

[51] Int. Cl.$^4$ ............................................. C07D 307/88
[52] U.S. Cl. .................................... 549/308; 549/309; 106/219
[58] Field of Search ................................ 549/308, 309

[56] References Cited

U.S. PATENT DOCUMENTS

| | | | |
|---|---|---|---|
| 2,597,965 | 4/1950 | Adams et al. | 549/309 |
| 2,742,483 | 4/1956 | Crounse | 549/309 |
| 3,185,709 | 5/1965 | Munro et al. | 549/309 |
| 3,491,112 | 1/1970 | Lin | 548/440 |
| 3,642,514 | 2/1972 | Orita et al. | 549/309 |
| 3,829,322 | 8/1974 | Ozutsumi et al. | 106/21 |

FOREIGN PATENT DOCUMENTS

| | | |
|---|---|---|
| 808535 | 12/1912 | Belgium . |
| 50-124930 | 10/1975 | Japan . |

OTHER PUBLICATIONS

Crounse et al. Chem. Abst. 81, 1974, 137594p.
Kondo et al., CA 84: 19192v.
Kast et al., CA vol. 83, 1975, 61715x.
Hughes et al., CA 140255f, vol. 76, 1972.
Bulletin de l'Academie des Sciences de l'URSS Classe des Sciencies Chemie 81–8 (1940) (C.A. 35 2488$^4$).
Journal American Chemical Society 82 5143–5147 (1960).
Journal of the Chemical Society 680–687 (1965).

*Primary Examiner*—Jane T. Fan
*Attorney, Agent, or Firm*—Terrence E. Miesle

[57] ABSTRACT

Process comprises the combination of the three steps of condensing 3-N(R)$_2$-4-X-benzoic acid with an aromatic or heterocyclic aldehyde, Y-CHO, under acidic conditions to produce 3-Y-5-X-6-N(R)$_2$phthalide (II), condensing said phthalide with a compound of the formula Z-H under alkaline or acid conditions to produce 2-($\alpha$-Y-$\alpha$-Z)methyl-4-X-5-N(R)$_2$benzoic acid (III), and oxidizing said benzoic acid to produce 3-Y-3-Z-5-X-6-N(R)$_2$phthalide (I) where: R is hydrogen, non-tertiary alkyl of one to four carbon atoms, benzyl or substituted benzyl; X is hydrogen or halo; Y is 4-R$^1$-3-R$^2$-2-R$^1$-phenyl, 1-R$^5$-2-R$^6$-5/6-R$^4$-3-indolyl, 9-R$^7$-3-carbazolyl, 9-julolidinyl, 3,4-dioxymethylenephenyl, 2-thienyl, 1-R$^8$-2-pyrrolyl, or 4-pyridinyl; and Z is 4-R$^1$-3-R$^2$-2-R$^1$-phenyl, 1-R$^5$-2-R$^6$-5/6-R$^4$-3-indolyl or 1-R$^8$-2-pyrrolyl which are useful as colorless precursor color formers in carbonless duplicating and in thermal marking systems. The intermediates, 3-Y-5-X-6-N(R)$_2$phthalides (II) and 2-($\alpha$-Y-$\alpha$-Z)methyl-4-X-5-N(R)$_2$benzoic acids (III) also have utility as colorless precursor color formers in carbonless duplicating and thermal marking systems.

3 Claims, No Drawings

SUBSTITUTED PHTHALIDES

CROSS REFERENCE TO RELATED APPLICATIONS

This application is a division of our prior copending application, Ser. No. 793,544 filed May 4, 1977 and now abandoned, which is a continuation-in-part of our prior copending application, Ser. No. 726,482, filed Sept. 24, 1976 and now abandoned.

BACKGROUND OF THE INVENTION (a) Field of the Invention

This invention relates to a novel three-step process for the preparation of 3,3-aryl- and/or heteryl-disubstituted phthalides useful in the art of carbonless duplicating as, for example, in pressure-sensitive systems and in thermal marking systems; and to novel 3-aryl- or heteryl-substituted phthalides and 2-($\alpha,\alpha$-aryl- and/or heteryl-distributed)methyl benzoic acid intermediates produced by said process.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides with which this invention is concerned, for example, crystal violet lactone; fluorans, for example, 2'-anilino-6'-diethylaminofluoran and 2'-dibenzylamino-6'-diethylaminofluoran; and various other types of colorless precursors currently employed in commercially accepted carbonless copy systems. Typical of the many such systems taught in the prior art are those described in U.S. Pat. Nos. 2,712,507, 2,800,457 and 3,041,289 which issued July 5, 1955, July 23, 1957 and June 26, 1962, respectively.

The following items to date appear to constitute the most relevant prior art with regard to the instant invention. Rodionov and Fedorova in the Bulletin de l'Academie des Sciences de l'URSS Classe des Sciences Chemie 81-8 (1940) [Chemical Abstracts 35: 2488$^4$ (1949)] describe the preparation of 3-aryl-substituted phthalides, for example, 3-(4-dimethylaminophenyl)phthalide, 3-(4-diethylaminophenyl)-6,7-dimethoxyphthalide and 3-(4-ethylmethylaminophenyl)-6,7-dimethoxy phthalide, by heating the appropriate N,N-dialkylaniline with the appropriate phthalaldehydic acid. The physical characteristics of the compounds are described without giving any indication as to their utility. Noland and Johnson in the Journal of the American Chemical Society 82, 5143–5147 (1960) describe the preparation of 3-heteryl-substituted phthalides, for example, 3-(1,2-dimethyl-3-indolyl)phthalide, 3-(2-methyl-3-indolyl)-6,7-dimethoxy phthalide and other isomers by fusing equimolar proportions of an indole and a phthalaldehydic acid. Physical data are given for the compounds and there is no indication of their utility. Rees and Sabet in the Journal of the Chemical Society, 680–687 (1965) describe the preparation and physical characteristics of 3-(3-indolyl)phthalide. There is no indication of the utility of the compound in the reference which is prepared by the acid-catalyzed interaction of indole and phthalaldehydic acid. In the same reference, Rees and Sabet describe the preparation and physical characteristics of $\alpha,\alpha$-di-(3-indolyl)-2-methylbenzoic acid prepared by the interaction of 3-(3-indolyl)phthalide with indole in refluxing alcoholic potassium hydroxide. No utility of the compounds is given in the reference.

U.S. Pat. Nos. 2,742,483 and 3,185,709, which issued Apr. 17, 1956 and May 25, 1965 respectively, disclose 2-[4,4'-bis-(dimethylamino)benzhydryl]-5-dimethylaminobenzoic acid which is obtained from the interaction of m-dimethylaminobenzoic acid and 4,4'-bis-(dimethylamino)benzhydrol. The compound is described as the intermediate to 3,3-bis(4-dimethylaminophenyl)-6-dimethylaminophthalide which according to the earlier patent, is obtained by permanganate oxidation and according to the later patent, by oxidation with molecular oxygen. The 3,3-bis(4-dimethylaminophenyl)-6-dimethylaminophthalide (crystal violet lactone) is well known as a colorless precursor for carbonless duplicating systems.

Belgian Pat. No. 808,535, granted Dec. 12, 1973, discloses 3-[2,4-bis(dimethylamino)phenyl]-3-(4-dimethylaminophenyl)-6-dimethylaminophthalide and similar compounds which are prepared by condensing the appropriate o-(4-dialkylaminobenzoyl)benzoic acid with the appropriate N,N,N',N'-tetraalkyl-m-phenylenediamine. These compounds are described as being useful as colorless precursors for carbonless duplicating systems.

U.S. Pat. No. 3,491,112, which issued Jan. 20, 1970, discloses 3-(4-dimethylaminophenyl)-3-(1,2-dimethyl-3-indolyl)-6-dimethylaminophthalide which is prepared by condensing 4,4'-bis(dimethylamino)benzophenone-2-carboxylic acid and 1,2-dimethylindole. The compound has utility as a colorless precursor for carbonless duplicating systems.

U.S. Pat. No. 3,829,322, which issued Aug. 13, 1974, discloses 3-(2-methyl-4-N-ethylbenzylaminophenyl)-3-(1-ethyl-2-methyl-3-indolyl)-6-dimethylaminophthalide which is prepared by interacting 1-ethyl-2-methyl-3-(4'-dimethylamino-2'-carboxybenzoyl)-indole and N-benzyl-N-ethyl-3-methylaniline. The compound has utility as a colorless precursor for carbonless duplicating systems.

(c) Prior Publication

Japanese Patent Publication No. Sho 50-124930, which was published on Oct. 1, 1975, describes a series of compounds having the formula

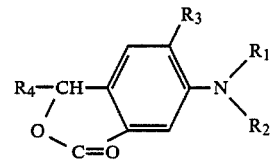

wherein each of $R_1$ and $R_2$ represents a hydrogen atom, a lower alkyl, haloalkyl, alkoxyalkyl, acyloxyalkyl, cyanoethyl, allyl, propargyl, cyclohexyl, benzyl or phenyl in which the benzene ring may be substituted by lower alkyl, halogen, nitro or lower alkoxyl radical, or $R_1$ and $R_2$ together may form a heterocyclic ring with the adjacent nitrogen atom; $R_3$ represents a hydrogen atom or chlorine atom; $R_4$ represents a benzene ring or heterocyclic ring which may be substituted. According to the reference, the compounds are prepared by the condensation of an appropriate aromatic aldehyde and an appropriate benzoic acid at an elevated temperature in the presence of a dehydrating agent and are described as colorless precursors in carbonless, pressure-sensitive and thermal copy systems. This reference appeared subsequent to applicant's invention described herein and less than one year prior to the filling date of this application.

SUMMARY OF THE INVENTION

In one of its process aspects, the invention relates to the three-step process for producing a 3-Y-3-Z-5-X-6-N(R)₂-phthalide which comprises condensing a 3-N(R)₂-4-X-benzoic acid with an aldehyde, Y—CHO, to produce a 3-Y-5-X-6-N(R)₂phthalide, condensing said phthalide with a compound, Z—H, to produce a 2-(α-Y-α-Z)methyl-4-X-5-N(R)₂benzoic acid, and oxidizing said benzoic acid to produce the 3-Y-3-Z-5-X-6-N(R)₂phthalide.

In a second of its process aspects, the invention relates to the process for producing a 3-Y-5-X-6-N(R)₂phthalide which comprises condensing a 3-N(R)₂-4-X-benzoic acid with an aldehyde, Y—CHO.

In a third of its process aspects, the invention relates to the two-step process for producing a 2-(α-Y-α-Z)-methyl-4-X-5-N(R)₂benzoic acid which comprises condensing a 3-N(R)₂-4-X-benzoic acid with an aldehyde, Y—CHO, to produce a 3-Y-5-X-6-N(R)₂phthalide, condensing said phthalide with a compound, Z—H, to produce said 2-(α-Y-α-Z)methyl-4-X-5-N(R)₂-benzoic acid.

In the fourth of its process aspects, the invention relates to the two-step process for producing a 3-Y-3-Z-5-X-6-N(R)₂phthalide which comprises condensing a 3-Y-5-X-6-N(R)₂-phthalide with a compound, Z—H, to produce a 2-(α-Y-α-Z)methyl-4-X-5-N(R)₂benzoic acid and oxidizing said benzoic acid to produce said 3-Y-3-Z-5-X-6-N(R)₂phthalide.

In one of its composition of matter aspects, the invention relates to certain 3-Y-3-Z-5-X-6-N(R)₂phthalides useful as colorless precursors in carbonless duplicating systems.

In a second composition of matter aspect, the invention relates to certain 3-Y-5-X-6-N(R)₂phthalides useful as intermediates in the processes of this invention and as colorless precursors in carbonless duplicating systems.

In a third composition of matter aspect, the invention relates to certain 2-(α-Y-α-Z)methyl-4-X-5-N(R)₂benzoic acids useful as intermediates in the processes of this invention and also as colorless precursors in carbonless duplicating systems.

In still another aspect, the invention relates to pressure-sensitive carbonless duplicating systems and/or to thermal marking systems which contain any of the above-mentioned 3-Y-3-Z-5-X-6-N(R)₂phthalides, 3-Y-5-X-6-N(R)₂phthalides or 2-(α-Y-α-Z)methyl-4-X-5-N(R)₂benzoic acids represented by Formulas I, II and III, respectively.

DETAILED DESCRIPTION INCLUSIVE OF THE PREFERRED EMBODIMENTS

More specifically, this invention in one of its process aspects, resides in the novel process consisting of three steps which comprises condensing a 3-N(R)₂-4-X-benzoic acid with an aromatic or heterocyclic aldehyde of the formula Y—CHO in the presence of an acid condensing agent under dehydrating conditions to produce a 3-Y-5-X-6-N(R)₂phthalide, condensing said phthalide with a compound of the formula Z—H in the presence of an alkaline or an acid condensing agent to produce a 2-(α-Y-α-Z)methyl-4-X-5-N(R)₂benzoic acid, and oxidizing said benzoic acid to produce a 3-Y-3-Z-5-X-6-N(R)₂phthalide having the formula

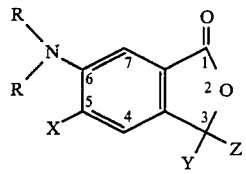

Formula I wherein R represents hydrogen, non-tertiary alkyl of one to four carbon atoms, benzyl or benzyl substituted in the benzene ring by one or two of halo or alkyl of one to three carbon atoms; X represents hydrogen or halo; Y represents a monovalent moiety selected from the class having the formulas

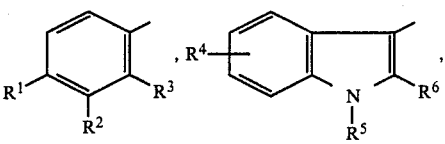

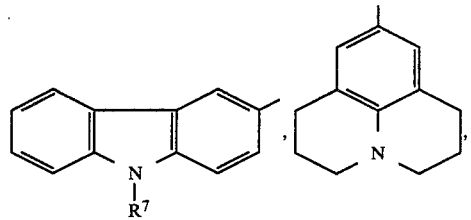

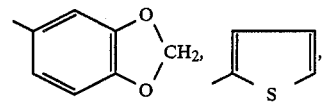

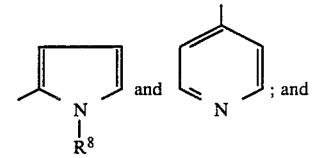

Z represents a monovalent moiety selected from the class having the formulas

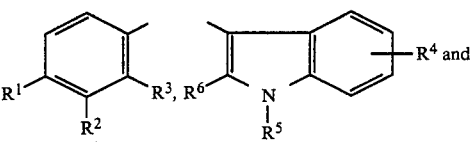

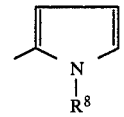

in which R¹ represents hydrogen, non-tertiary alkoxy of one to four carbon atoms, dialkylamino or N-alkylbenzylamino in which alkyl is non-tertiary alkyl of one to four carbon atoms, R² represents hydrogen, alkyl of one to three carbon atoms or non-tertiary alkoxy of one to four carbon atoms, R³ represents hydrogen, alkyl of one to three carbon atoms, non-tertiary alkoxy of one to four carbon atoms, halo or dialkylamino in which alkyl is non-tertiary alkyl of one to four carbon atoms, $R^4$ represents one or two of hydrogen, alkyl of one to three carbon atoms, alkoxy of one to three carbon atoms, halo or nitro, $R^5$ represents hydrogen, non-tertiary alkyl of one to eight carbon atoms, alkenyl of two to four carbon atoms, benzyl or benzyl substituted in the benzene ring by one or two halo or alkyl of one to three carbon atoms, $R^6$ represents hydrogen, alkyl of one to three carbon atoms or phenyl, and $R^7$ and $R^8$ represent hydrogen or alkyl of one to three carbon atoms.

This invention, in a second of its process aspects, resides in the novel process which comprises condensing a 3-N(R)$_2$-4-X-benzoic acid with an aromatic or heterocyclic aldehyde of the formula Y—CHO in the presence of an acid condensing agent under dehydrating conditions to produce a 3-Y-5-X-6-N(R)$_2$-phthalide having the formula

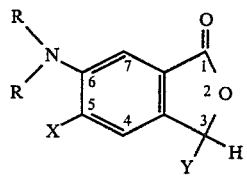

Formula II wherein R, X and Y have the same respective meanings indicated in Formula I.

This invention, in a third of its process aspects, resides in the novel process consisting of two steps which comprises condensing a 3-N(R)$_2$-4-X-benzoic acid with an aromatic or heterocyclic aldehyde of the formula Y—CHO in the presence of an acid condensing agent under dehydrating conditions to produce a 3-Y-5-X-6-N(R)$_2$phthalide of Formula II and condensing said phthalide with a compound of the formula Z-H in the presence of an alkaline or an acid condensing agent to produce a 2-(α-Y-α-Z)methyl-4-X-5-N(R)$_2$benzoic acid having the formula

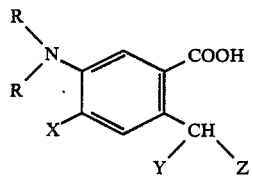

Formula III wherein R, X, Y and Z have the same respective meanings indicated in Formula I.

This invention, in a fourth of its process aspects, resides in the novel process consisting of two steps which comprises condensing a 3-Y-5-X-6-N(R)$_2$phthalide of Formula II with a compound of the formula Z—H in the presence of an alkaline or an acid condensing agent to produce a 2-(α-Y-α-Z)methyl-4-X-5-N(R)$_2$benzoic acid of Formula III, and oxidizing said benzoic acid to produce a 3-Y-3-Z-5-X-6-N(R)$_2$phthalide of Formula I wherein R, X, Y and Z have the same respective meanings indicated in Formula I.

In one of its composition of matter aspects, this invention resides in the novel 3-Y-5-X-6-N(R)$_2$phthalides of Formula II wherein R, X and Y have the same respective meanings indicated in relation to Formula II which are useful as intermediates in the processes of this invention and are also useful as color precursors in carbonless duplicating and in thermal marking systems.

In a first particular embodiment in accordance with its phthalide intermediate aspect, the invention sought to be patented resides in the novel 3-(2-R$^3$-3-R$^2$-4-R$^1$-phenyl)-5-X-6-N(R)$_2$phthalides. Preferred compounds within the ambit of this particular embodiment are of the formula

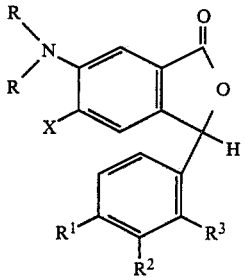

wherein R, R$^1$, R$^2$, R$^3$ and X each have the same respective meanings indicated in relation to Formula II.

In a second particular embodiment in accordance with its phthalide intermediate aspect, the invention sought to be patented resides in the novel 3-(1-R$^5$-2-R$^6$-5/6-R$^4$-3-indolyl)-5-X-6-N(R)$_2$phthalides. Preferred compounds within the ambit of this particular embodiment are of the formula

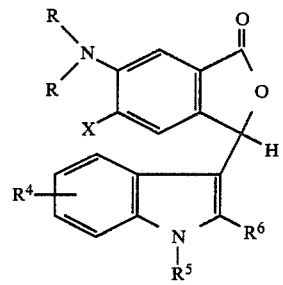

wherein R, R$^4$, R$^5$, R$^6$ and X have the same respective meanings given in relation to Formula II.

In a third particular embodiment in accordance with its phthalide intermediate aspect, the invention sought to be patented resides in the novel 3-(9-R$^7$-3-carbazolyl)-5-X-6-N(R)$_2$phthalides. Preferred compounds within the ambit of this particular embodiment are of the formula

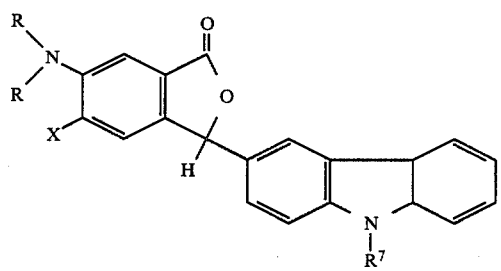

wherein R, R$^7$ and X each have the same respective meanings given in relation to Formula II.

In a fourth particular embodiment in accordance with its phthalide intermediate aspect, the invention sought to be patented resides in the novel 3-(9-julolidinyl)-5-X-6-N(R)$_2$-phthalides. Preferred compounds within the ambit of this particular embodiment are of the formula

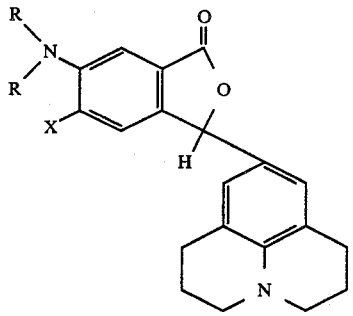

wherein R and X have the same respective meanings given in relation to Formula II.

In a fifth particular embodiment in accordance with its phthalide intermediate aspect, the invention sought to be patented resides in the novel 3-(3,4-methylenedioxyphenyl)-5-X-6-N(R)$_2$phthalides. Preferred compounds within the ambit of this particular embodiment are of the formula

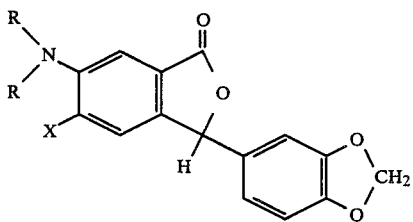

wherein R and X have the same respective meanings given in relation to Formula II.

In a sixth particular embodiment in accordance with its phthalide intermediate aspect, the invention sought to be patented resides in the novel 3-(2-thienyl)-5-X-6-N(R)$_2$phthalides. Preferred compounds within the ambit of this particular embodiment are of the formula

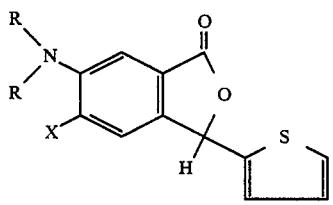

wherein R and X have the same respective meanings given in relation to Formula II.

In a seventh particular embodiment in accordance with its phthalide intermediate aspect, the invention sought to be patented resides in the novel 3-(1-R$^8$-2-pyrrolyl)-5-X-6-N(R)$_2$-phthalides. Preferred compounds within the ambit of this particular embodiment are of the formula

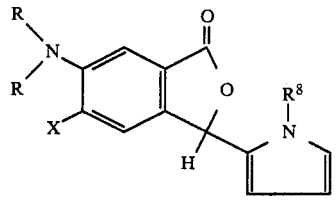

wherein R, R$^8$ and X have the same respective meanings given in relation to Formula II.

This invention, in a second of its composition of matter aspects, relating to intermediates, resides in the novel 2-($\alpha$-Y-$\alpha$-Z)methyl-4-X-5-N(R)$_2$benzoic acids of Formula III wherein R, X, Y and Z each have the same respective meanings given in relation to Formula III which are useful as intermediates in the processes of this invention and are also useful as color precursors in carbonless duplicating and in thermal marking systems.

In a first particular embodiment in accordance with its benzoic acid intermediate aspect, the invention sought to be patented resides in the novel 2-(2-R$^3$-3-R$^2$-4-R$^1$-2'-R$^3$-3'-R$^2$-4'-R$^1$-benzhydryl)-4-X-5-N(R)$_2$benzoic acids. Preferred compounds within the ambit of this particular embodiment are of the formula

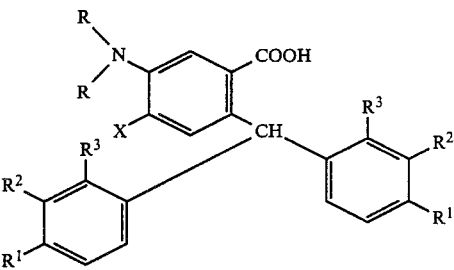

wherein R, R$^1$, R$^2$, R$^3$ and X have the same respective meanings given in relation to Formula III.

In a second particular embodiment in accordance with its benzoic acid intermediate aspect, the invention sought to be patented resides in the novel 2-[$\alpha$-(2-R$^3$-3-R$^2$-4-R$^1$-phenyl)-$\alpha$-(1-R$^5$-2-R$^6$-5/6-R$^4$-3-indolyl)]methyl-4-X-5-N(R)$_2$benzoic acids. Preferred compounds within the ambit of this particular embodiment are of the formula

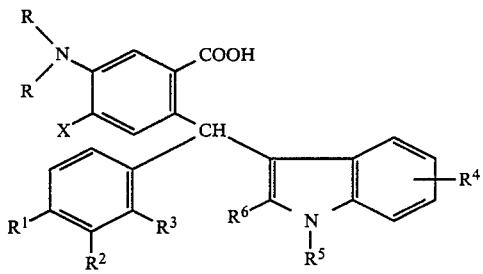

wherein R, R$^1$, R$^2$, R$^3$, R$^4$, R$^5$, R$^6$ and X have the same respective meanings given in relation to Formula III.

In a third particular embodiment in accordance with its benzoic acid intermediate aspect, the invention sought to be patented resides in the novel 2-[$\alpha$-(2-R$^3$-3-R$^2$-4-R$^1$-phenyl)-$\alpha$-(1-R$^8$-2-pyrrolyl)]methyl-4-X-5-N(R)$_2$benzoic acids. Preferred compounds within the ambit of this particular embodiment are of the formula

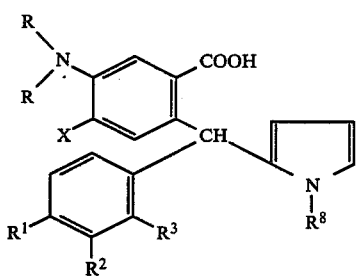

wherein R, $R^1$, $R^2$, $R^3$, $R^8$ and X have the same respective meanings given in relation to Formula III.

This invention, in a third of its composition of matter aspects, relating to final products produced by the processes of this invention, resides in the novel 3-Y-3-Z-5-X-6-N(R)$_2$phthalides of Formula I wherein R, X, Y and Z each have the same respective meanings given in relation to Formula I which are useful as colorless precursors in carbonless or thermal duplicating systems.

In a first particular embodiment in accordance with its final products aspect, the invention sought to be patented resides in the novel 3-(2-$R^{3'}$-4-$R^{1'}$-phenyl)-3-(2-$R^3$-3-$R^{2'}$-4-$R^{1''}$-phenyl)-5-X-6-N(R)$_2$phthalides, which are particularly useful as colorless precursors in the art of carbonless duplicating and having the formula

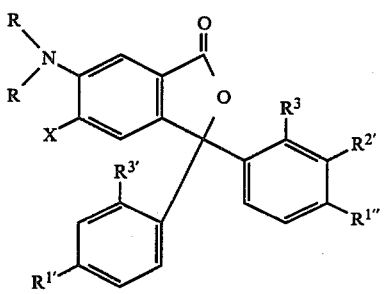

Formula IV wherein R represents non-tertiary alkyl of one to four carbon atoms; $R^{1'}$ represents hydrogen, non-tertiary alkoxy of one to four carbon atoms, N-alkylbenzylamino in which alkyl is non-tertiary alkyl of one to four carbon atoms or, when $R^3$ is other than dialkylamino, dialkylamino in which alkyl is non-tertiary alkyl of one to four carbon atoms; $R^{1''}$ represents dialkylamino in which alkyl is non-tertiary alkyl of one to four carbon atoms; $R^{2'}$ represents hydrogen or alkyl of one to three carbon atoms; $R^3$ represents hydrogen, alkyl of one to three carbon atoms, non-tertiary alkoxy of one to four carbon atoms, halo or dialkylamino in which alkyl is non-tertiary alkyl of one to four carbon atoms; $R^{3'}$ represents hydrogen, alkyl of one to three carbon atoms, non-tertiary alkoxy of one to four carbon atoms or halo; X represents hydrogen or halo; and with the proviso that $R^{2'}$, $R^3$, $R^{3'}$ and X cannot all be hydrogen at the same time.

In a second particular embodiment in accordance with its final products aspect, the invention sought to be patented resides in the novel 3-(2-$R^{3''}$-3-$R^{2''}$-4-$R^{1'}$-phenyl)-3-(1-$R^5$-2-$R^6$-5/6-$R^4$-3-indolyl)-5-X-6-N(R)$_2$phthalides, which are particularly useful as colorless precursors in the art of carbonless duplicating and having the formula

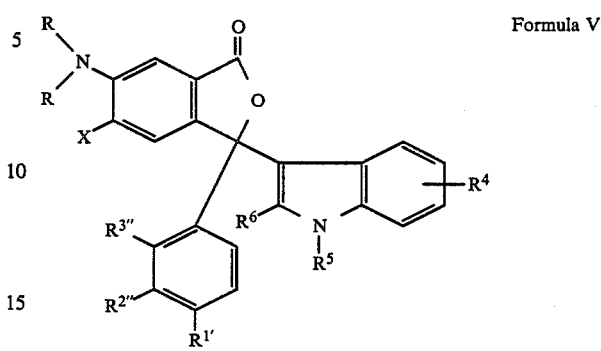

Formula V wherein R represents non-tertiary alkyl of one to four carbon atoms; $R^{1'}$ represents hydrogen, non-tertiary alkoxy of one to four carbon atoms, N-alkylbenzylamino in which alkyl is non-tertiary alkyl of one to four carbon atoms or, when at least one of $R^{2''}$ and $R^{3''}$ are other than hydrogen, dialkylamino in which alkyl is non-tertiary alkyl of one to four carbon atoms; $R^{2''}$ and $R^{3''}$ each represent hydrogen, non-tertiary alkoxy of one to four carbon atoms or halo; $R^4$ represents one or two of hydrogen, alkyl of one to three carbon atoms, alkoxy of one to three carbon atoms, halo or nitro; $R^5$ represents hydrogen, non-tertiary alkyl of one to eight carbon atoms, alkenyl of two to four carbon atoms, benzyl or benzyl substituted in the benzene ring by one or two of halo or alkyl of one to three carbon atoms; $R^6$ represents hydrogen, alkyl of one to three carbon atoms or phenyl; and X represents hydrogen or halo.

As used herein, the term "non-tertiary alkyl of one to eight carbon atoms" means saturated monovalent aliphatic radicals, including branched chain radicals, for example, methyl, ethyl, propyl, isopropyl, butyl, isobutyl, amyl, 1-methylbutyl, 3-methylbutyl, hexyl, isohexyl, heptyl, isoheptyl, octyl, isooctyl and 2-ethylhexyl.

When the terms "alkyl of one to three carbon atoms", "alkoxy of one to three carbon atoms" and "non-tertiary alkoxy of one to four carbon atoms" are used herein, there is meant saturated, acyclic groups which may be straight or branched as exemplified by methyl, ethyl, propyl, isopropyl, methoxy, ethoxy, propoxy, isopropoxy, butoxy, sec-butoxy, and isobutoxy.

As used herein, the term "alkenyl of two to four carbon atoms" means a monovalent aliphatic radical possessing a single double bond, for example, ethenyl (or vinyl), 2-propenyl (or allyl), 1-methylethenyl (or isopropenyl), 2-methyl-2-propenyl, 2-methyl-1-propenyl, 2-butenyl and 3-butenyl.

When the term "halo" is used herein, there are included chloro, fluoro, bromo and iodo. The preferred halo substituent is chloro because the other halogens offer no particular advantages over chloro and because of the relatively low cost and ease of preparation of the required chloro intermediates. However, the other above-named halo substituents are also satisfactory.

The term "N-alkylbenzylamino" as used herein, means an amino radical substituted by an alkyl substituent and a benzyl substituent in which the benzene ring may be unsubstituted or substituted by one or two of halo or alkyl of one to three carbon atoms.

As used herein, the term "alkaline condensing agent" is intended to be inclusive of both inorganic and organic basic compounds as exemplified hereinafter.

The compounds depicted by Formula III have been designated as 2-($\alpha$-Y-$\alpha$-Z)methyl-4-X-5-N(R)$_2$benzoic acids. This nomenclature defines compounds of Formula III in which the methyl group in the 2-position can bear two aromatic moieties, two heterocyclic moieties or one aromatic and one heterocyclic moiety. However, throughout this specification, whenever possible, those species defined by Formula III having two phenyl moieties attached to the 2-methyl carbon atom have been named by using the more conventional "benzhydryl" designation for diphenylmethyl groups.

The processes of this invention afford a novel convenient and economically advantageous synthetic route to a large number of both known and novel compounds as final products which are 3,3-disubstituted phthalides of the type represented by Formula I. Many species defined by Formula I are well-known to be useful as colorless precursors in carbonless duplicating systems, for example, 3,3-bis(4-dimethylaminophenyl)-6-dimethylaminophthalide or, as this compound has been more simply designated, crystal violet lactone, 3-(4-dimethylaminophenyl)-3-(1,2-dimethyl-3-indolyl)-6-dimethylaminophthalide described in U.S. Pat. No. 3,491,112, 3-[2,4-bis(dimethylamino)phenyl]-3-(4-dimethylaminophenyl)-6-dimethylaminophthalide described in Belgian Pat. No. 808,535, and the like.

The processes of this invention also afford 3-substituted phthalides of the type represented by Formula II and 2-($\alpha$,$\alpha$-disubstituted)methyl benzoic acids of the type represented by Formula III. The 3-substituted phthalides of Formula II are useful as intermediates to the 2-($\alpha$,$\alpha$-disubstituted)methylbenzoic acids of Formula III which in turn are useful as intermediates to the final products depicted by Formula I. Moreover, both the 3-substituted phthalides of Formula II and the 2-($\alpha$,$\alpha$-disubstituted)methyl benzoic acids of Formula III have been found to be useful as color precursors in pressure-sensitive carbonless duplicating systems and in thermal marking systems.

The novel compounds represented by Formulas I, II and III above are essentially colorless in the depicted form. When the compounds of Formulas I, II and III are contacted with an acidic medium for example, silica gel or one of the types regularly employed in pressure-sensitive carbonless duplicating systems, for example, silton clay or phenolic resins, they develop a colored image of good to excellent tinctorial strength. The development of color on contact with silica gel, silton clay or a phenolic resin demonstrates that these compounds are highly suitable for use as colorless precursors, that is, color-forming substances in pressure-sensitive carbonless duplicating systems. For such application, the compounds may be incorporated in any of the commercially accepted systems known in the carbonless duplicating art. A typical technique for such application is as follows. Solutions of the colorless precursor compounds in suitable aromatic solvents are microencapsulated by well-known procedures. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a bluish-green to reddish-purple colored image of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold.

It has also been found that when the compounds of Formulas I, II and III are intimately mixed with an acidic developer of the type generally employed in thermal papers, that is, papers which produce a colored image when contacted with a heated stylus or heated type, for example, bisphenol A, heating of the mixture produces a colored image of varying shades from yellow to purple depending on the particular compound of the invention employed. The ability of the compounds of Formulas I, II and III to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

In view of the utility of the novel compounds represented by Formulas II, III, IV and V as described above, another aspect of this invention resides in pressure-sensitive carbonless duplicating systems and thermal paper marking systems containing as a color-forming substance any of the 3-Y-5-X-6-N(R)$_2$-phthalides depicted by Formula II; the 2-($\alpha$-Y-$\alpha$-Z)methyl-4-X-5-N(R)$_2$benzoic acids depicted by Formula III; the 2-(2-R$^{3'}$-4-R$^{1'}$-phenyl)-3-(2-R$^3$-3-R$^{2'}$-4-R$^{1''}$-phenyl)-5-X-6-N(R)$_2$phthalides depicted by Formula IV; and the 3-(2-R$^{3''}$-3-R$^{2''}$-4-R$^{1'}$-phenyl)-3-(1-R$^5$-2-R$^6$-5/6-R$^4$-3-indolyl)-5-X-6-N(R)$_2$phthalides depicted by Formula V wherein R, R$^1$, R$^{1'}$, R$^{1''}$, R$^2$, R$^{2'}$, R$^{2''}$, R$^3$, R$^{3'}$, R$^{3''}$, R$^4$, R$^5$, R$^6$, X, Y and Z have the same respective meanings given in relation to Formulas II, III, IV and V.

The best mode contemplated by the inventors of carrying out this invention will now be described as to enable any person skilled in the art to which it pertains to make and use the same.

The 3-Y-5-X-6-N(R)$_2$phthalides of Formula II, which are produced in the first step of the instant process, are obtained by interacting approximately an equimolar quantity of an appropriate aromatic or heterocyclic aldehyde with an appropriate benzoic acid in the presence of an acid condensing agent. The reaction is conveniently carried out in a dehydrating solvent which also serves as an acid condensing agent, for example, acetic anhydride, a mixture of acetic anhydride and acetic acid, and acid chloride such as phosphorus oxychloride, or in a mineral acid, preferably concentrated hydrochloric acid at a temperature in the range of 80° to 140° C., but more desirably, at the reflux temperature of the solvent. The 3-Y-5-X-6-N(R)$_2$-phthalide thus obtained can generally be isolated by filtration from the reaction medium. Alternatively, a miscible nonsolvent, for example, a short chain aliphatic alcohol can be added to the reaction medium before filtration. The isolated product is dried by conventional means.

The various aminobenzoic acids required as starting materials for the first step of the instant processes in which the products of Formula II are obtained form an old and well-known class of compounds which are either commercially available or are readily obtained by conventional procedures well known in the art. The following compounds are exemplary of aminobenzoic acids useful in the first step of the processes of this invention to obtain 3-Y-5-X-6-N(R)$_2$phthalides of Formula II.
3-Aminobenzoic acid,
3-Amino-4-chlorobenzoic acid,
3-Dimethylaminobenzoic acid,
3-Methylaminobenzoic acid,
3-(N-Ethyl-N-methylamino)benzoic acid,
3-Ethylamino-4-bromobenzoic acid,
3-(N-Ethyl-N-butylamino)benzoic acid,
3-Diethylaminobenzoic acid,
3-(N-Ethylbenzylamino)benzoic acid,
3-Dibenzylaminobenzoic acid,
3-Propylamino-4-fluorobenzoic acid,
3-Diethylamino-4-iodobenzoic acid,
3-Ethylaminobenzoic acid,
3-Dimethylamino-4-chlorobenzoic acid,
3-[N-Butyl-N-(4-chlorobenzyl)amino]benzoic acid, and
3-[N-Methyl-N-(4-methylbenzyl)amino]benzoic acid.

The aromatic and heterocyclic aldehydes required as starting materials for the first step of the instant processes in which the 3-Y-5-X-6-N(R)$_2$phthalides of Formula II are obtained constitute an old and well-known class of compounds many of which are commercially available or are readily obtained by conventional syntheses well known in the art. The following list of compounds exemplifies aromatic and heterocyclic aldehydes useful in carrying out the first step of the processes of this invention leading to the compounds of Formula I.
Benzaldehyde,
2-Methylbenzaldehyde,
2-Chlorobenzaldehyde,
2-Methoxybenzaldehyde,
3-Methoxybenzaldehyde,
4-Methoxybenzaldehyde,
2-Bromobenzaldehyde,
2-Ethoxybenzaldehyde,
3-Ethoxybenzaldehyde,
4-Ethoxybenzaldehyde,
2-Fluorobenzaldehyde,
4-Isopropylbenzaldehyde,
2,3-Dimethoxybenzaldehyde,
2,4-Dimethoxybenzaldehyde,
2,5-Dimethoxybenzaldehyde,
3,4-Dimethoxybenzaldehyde,
3,5-Dimethoxybenzaldehyde,
2-Butoxy-4-diethylaminobenzaldehyde,
2-Methyl-4,5-dimethoxybenzaldehyde,
2-Chloro-4-dimethylaminobenzaldehyde,
3-Ethoxy-4-methoxybenzaldehyde,
2,3,4-Trimethoxybenzaldehyde,
2-Methoxy-4-dimethylaminobenzaldehyde,
2-Methoxy-4-diethylaminobenzaldehyde,
4-Dimethylaminobenzaldehyde,
4-Benzylaminobenzaldehyde,
5-Methoxyindole-3-carboxaldehyde,
4-(N-Methylbenzylamino)benzaldehyde,
Indole-3-carboxaldehyde,
N-Methylpyrrole-2-carboxaldehyde,
2-Pyridinecarboxaldehyde,
3-Pyridinecarboxaldehyde,
4-Pyridinecarboxaldehyde,
Pyrrole-2-carboxaldehyde,
2-thiophenecarboxaldehyde,
N-Ethyl-3-carbazolecarboxaldehyde,
Piperonal,
2-Methyl-1-n-octylindole-3-carboxaldehyde,
1-n-Butyl-2-phenylindole-3-carboxaldehyde,
9-Formyljulolidine,
4-(N-Ethylbenzylamino)benzaldehyde,
2-Methyl-4-(N-methylbenzylamino)benzaldehyde,
1,2-Dimethylindole-3-carboxaldehyde,
1-Ethyl-2-phenylindole-3-carboxaldehyde,
4-Diethylaminobenzaldehyde,
2-Methyl-4-diethylaminobenzaldehyde, and
1-Ethyl-2-methylindole-3-carboxaldehyde.

The 2-($\alpha$-Y-$\alpha$-Z)methyl-4-X-5-N(R)$_2$benzoic acids of Formula III are prepared by interacting approximately an equimolar quantity of an appropriate 3-Y-5-X-6-N(R)$_2$phthalide of Formula II with an appropriate aromatic or heterocyclic compound of the formula Z—H wherein Z is defined in the same manner as in relation to Formulas I and III. In one set of reaction conditions, the 3-substituted phthalide and the aromatic or heterocyclic compound are interacted in the presence of an alkaline condensing agent, in dilute aqueous solution at a temperature of 90°–160° C. The 2-($\alpha$-Y-$\alpha$-Z)methyl-4-X-5-N(R)$_2$-benzoic acid of Formula III thus formed can optionally be isolated by carefully neutralizing the alkaline or basic reaction solution with dilute aqueous acid, collecting the separated product by filtration, and drying the solid by conventional means. Alternatively, the alkaline or basic reaction solution containing the 2-($\alpha$-Y-$\alpha$-Z)methyl-4-X-5-N(R)$_2$benzoic acid of Formula III in the form of a salt can be used directly in the next step of the overall processes without isolation of the product in the free-acid form.

The following basic inorganic and organic compounds are exemplary of "alkaline condensing agents" useful in the second step of the processes of this invention to obtain 2-($\alpha$-Y-$\alpha$-Z)methyl-5-N(R)$_2$benzoic acids of Formula III: sodium hydroxide, potassium hydroxide, lithium hydroxide, sodium carbonate, potassium carbonate, lithium carbonate, ammonium hydroxide, tetramethylammonium hydroxide, tetraethylammonium hydroxide, tetrabutylammonium hydroxide, quinuclidine, 1,4-diazobicyclo[2,2,2]octane, triethanolamine, and triethylamine.

In a second set of reaction conditions, the interaction of an equimolar quantity of an appropriate 3-Y-5-X-6-N(R)$_2$phthalide of Formula II and an appropriate aromatic or heterocyclic compound of formula Z—H can be carried out in the presence of an acid condensing agent, for example, an organic or inorganic acid at a temperature in the range of 70°–120° C. The 2-($\alpha$-Y-$\alpha$-Z)methyl-4-X-5-N(R)$_2$benzoic acid of Formula III thus produced is then isolated by adding the reaction solution to water, chilling the resultant mixture and collecting the separated product by filtration followed by drying it by conventional methods.

The following compounds are exemplary of organic and inorganic acids useful as "acid condensing agents" in the second step of the processes of this invention to obtain 2-($\alpha$-Y-$\alpha$-Z)methyl-5-benzoic acids of Formula III: formic acid, acetic acid, propionic acid, glycolic acid, oxalic acid, citric acid, methanesulfonic acid, toluenesulfonic acid, phosphoric acid, polyphosphoric acid, hydrofluoric acid, hydrochloric acid, hydrobromic acid, phosphorus oxychloride, phosphorus tribromide, phosphorus trichloride, and phosphorus pentachloride.

In still a third set of reaction conditions, the 2-(α-Y-α-Z)methyl-4-X-5-N(R)₂benzoic acids of Formula III are obtained by the interaction of approximately an equimolar quantity of an appropriate 3-Y-5-X-6-N(R)₂phthalide of Formula II and an appropriate aromatic or heterocyclic compound of formula Z—H. The reaction is conveniently carried out in the presence of an acid condensing agent of the type generally defined as a Friedel-Craft catalyst in the presence of an inert organic solvent, for example, monochlorobenzene, ethylene dichloride, perchloroethylene, carbon tetrachloride, nitrobenzene, and so forth or optionally in the presence of an excess amount of reactant Z—H as the solvent at a temperature in the range of −10° to 110° C. When an inert organic solvent is employed, the 2-(α-Y-α-Z)methyl-4-X-5-N(R)₂benzoic acid thus formed is isolated by extracting the acid condensing agent with water from the organic phase followed by extraction of the 2-(α-Y-α-Z)methyl-4-X-5-N(R)₂benzoic acid from the organic layer with dilute aqueous hydrochloric acid. The product is obtained by neutralizing the aqueous acid solution with a dilute aqueous solution of a base, for example, sodium hydroxide, collecting the separated product by filtration, and drying it by conventional means. Alternatively, when excess Z—H is used as the solvent, the 2-(α-Y-α-Z)methyl-4-X-5-N(R)₂-benzoic acid formed is isolated by diluting the reaction mixture with water, rendering it basic by adding a dilute aqueous solution of a base, for example, sodium hydroxide and then steam-distilling the excess Z—H away from the mixture. After the removal of excess Z—H is complete, the mixture is slightly cooled and the pH adjusted to approximately 4.9 by the addition of an acid, for example, acetic acid. The separated product is collected by filtration, washed with water and dried by conventional means.

The following compounds are exemplary of Friedel-Craft catalysts useful as acid condensing agents in the second step of the processes of this invention for the production of 2-(α-Y-α-Z)methyl-4-X-5-N(R)₂benzoic acids of Formula III: aluminum chloride, aluminum bromide, zinc chloride, zinc bromide, boron trifluoride, boron trichloride, boron tribromide, titanium tetrachloride, stannic chloride, stannic bromide, antimony trichloride, ferric fluoride, ferric chloride, ferric bromide, ferric iodide, phosphorus tribromide, phosphorus trichloride, and phosphorus pentachloride.

When ferric halide salts are employed as acid condensing agents in the interaction of 3-Y-5-X-6-N(R)₂phthalides with an excess of Z—H, final products, that is, 3-Y-3-Z-5-X-6-N(R)₂-phthalides are obtained in significant quantitites as well as the corresponding precursor intermediates, 2-(α-Y-α-Z)methyl-4-X-5-N(R)₂benzoic acids. It appears that a significant quantity of the 2-(α-Y-α-Z)methyl-4-X-5-N(R)₂benzoic acid resulting from the condensation of the 3-Y-5-X-6-N(R)₂phthalide interacted with the Z—H, is oxidized in situ to the 3-Y-3-Z-5-X-6-N(R)₂phthalide in the presence of the ferric halide salts.

The aromatic and heterocyclic compounds represented by the formula Z—H, which are required for interaction with the 3-Y-5-X-6-N(R)₂phthalides of Formula II to obtain the 2-(α-Y-α-Z)methyl-4-X-5-N(R)₂benzoic acids of Formula III form old and well-known classes of compounds readily obtained by conventional procedures well known in the art. The following list of compounds exemplifies aromatic and heterocyclic compounds falling within the ambit of the formula Z—H which are useful in the practice of the step in the processes of this invention for producing the aforesaid benzoic acids of Formula III.

N,N,N',N'-Tetramethyl-m-phenylenediamine,
N,N-Dibutylaniline,
N,N-Diethyl-3-ethoxyaniline,
N,N-Diethyl-m-anisidine,
N,N-Dimethylaniline,
N-Benzyl-N-ethylaniline,
N,N-Diethyl-m-toluidine
N,N-Diethylaniline,
N-Ethyl-N-methylaniline,
N-Benzyl-N-methylaniline,
N-Benzyl-N-propylaniline,
N,N-Dimethyl-3-bromoaniline,
N,N,N',N'-Tetraisopropyl-m-phenylenediamine,
N,N-Dibutyl-3-fluoroaniline,
N,N-Diethyl-2-methoxy-3-chloroaniline,
N-Benzyl-N-methyl-3-ethylaniline,
N,N,N',N'-Tetra-sec-butyl-m-phenylenediamine,
N-Benzyl-N-butyl-3-iodoaniline,
N,N-Diisopropyl-3-chloroaniline,
N-Benzyl-N-sec-butylaniline,
N,N-Di-sec-butylaniline,
N,N-Diethyl-3-isopropylaniline,
N,N-Diisobutylaniline,
N,N-Diethyl-2-propoxyaniline,
N,N-Dipropylaniline,
N-Isopropyl-N-methylaniline,
N-Methyl-N-propylaniline,
N,N,N',N'-Tetrabutyl-m-phenylenediamine,
N,N-Dipropyl-o-anisidine,
N-Isobutyl-N-ethylaniline,
N,N,N',N'-Tetraethyl-m-phenylenediamine,
N-Propyl-N-ethylaniline,
N,N-Diethyl-2-ethoxyaniline,
N-Benzyl-N-sec-butyl-2-propoxyaniline,
N,N-Dimethyl-m-toludine,
Indole,
1-Methylindole,
2-Methylindole,
1,2-Dimethylindole,
1-Ethyl-2-methylindole,
2-Phenylindole, 1-Propyl-2-methylindole,
1-Benzyl-2-methylindole,
1-Butyl-2-methylindole,
1-Octyl-2-methylindole,
2-Ethyl-5-methylindole,
1-Benzyl-5-fluoroindole,
1-Methyl-6-nitroindole,
5-Methoxy-1-butylindole,
1-Allyl-2-methylindole,
1,2-Dimethyl-6-nitroindole,
1-(4-Chlorobenzyl)-2-methyl-5-nitroindole,
2-Ethylindole,
2-Ethyl-1-methylindole,
1-Isopropylindole,
2-Isopropylindole,
1-Methyl-5-bromo-6-nitroindole,
2,5,6-Trimethylindole,
1-Isobutyl-2-methylindole,
6-Bromo-2-methylindole,
1-Hexylindole,
1-(2,5-Dimethylbenzyl)-2-methylindole,
2-Propylindole,
6-Chloro-2-phenylindole,
1-(2-Ethylhexyl)-2-methylindole,
1-(2,6-Dichlorobenzyl-2-methylindole,
1-Vinyl-2-methylindole, 2-Ethyl-6-methylindole,
6-Fluoro-1-benzylindole,
1-(4-Bromobenzyl)-2-isopropylindole,
1-(3-Chlorobenzyl)-2-ethylindole,
5-Chloro-1-benzylindole,
1-(2-Fluorobenzyl)-2-methylindole,
5-Iodo-1-(1-methylhexyl)indole,
5,6-Dimethoxyindole,
1-(2-Methylbenzyl)-2-methylindole,
5,6-Dichloro-2-phenylindole,
1-Isoamylindole,
1-[3-(2-Methyl)-1-propenyl]-2-methylindole,
Pyrrole,
N-Methylpyrrole,
N-Ethylpyrrole,
N-Propylpyrrole, and
N-Isopropylpyrrole.

The 3-Y-3-Z-5-X-6-N(R)$_2$phthalides of Formula I are obtained by oxidizing the appropriate 2-($\alpha$-Y-$\alpha$-Z)methyl-4-X-5-N(R)$_2$benzoic acids of Formula III. The oxidation is conveniently carried out in aqueous alkaline solutions, for example, potassium hydroxide, at a temperature in the range of 20°–160° C., but more desirably at 80°–160° C. The oxidizing agent can be molecular oxygen either in the form of gaseous oxygen or air. Alternatively, a chemical oxidizing agent, for example, potassium permanganate or hydrogen peroxide may be employed. Dependent on the temperature chosen, the oxidation is carried out either at atmospheric or superatmospheric pressures. The 3-Y-3-Z-5-X-6-N(R)$_2$phthalide thus produced is separated by filtration and dried by conventional means.

Alternatively, it has been found that the 3-Y-3-Z-5-X-N(R)$_2$phthalides of Formula I can be conveniently obtained in satisfactory yields without separate isolation and oxidation of the 2-($\alpha$-Y-$\alpha$-Z)methyl-4-X-5-N(R)$_2$benzoic acids of Formula III by carrying out the interaction of the appropriate 3-Y-5-X-6-N(R)$_2$phthalide with an excess of reactant Z-H in the presence of a ferric halide as the acid condensing agent and using the reaction conditions described hereinabove. The desired 3-Y-3-Z-5-X-6-N(R)$_2$phthalide obtained by this "telescoped" procedure is isolated by drowning the reaction mixture in dilute aqueous solution of a strong base, for example, sodium hydroxide, steam distilling away the excess Z-H, cooling to approximately 70° C., extracting the residue with a water-insoluble organic solvent, for example, toluene and filtering the mixture to remove any insolubles. The organic layer containing the 3-Y-3-Z-5-X-6-N(R)$_2$phthalide is separated from the alkaline aqueous phase which contains unoxidized 2-($\alpha$-Y-$\alpha$-Z)methyl-4-X-5-N(R)$_2$benzoic acid, generally in small amounts. The desired phthalide is then isolated by concentrating the organic layer by evaporation or distillation, collecting the solid by filtration, followed by drying by conventional means.

The molecular structures of the compounds of this invention were assigned on the basis of the modes of synthesis and study of their infrared, nuclear magnetic resonance, and mass spectra and elemental analysis.

The following examples will further illustrate the invention without, however, limiting it thereto. All melting points are uncorrected.

EXAMPLE 1

A. A stirred mixture of 306.0 g of acetic anhydride, 200.0 ml of glacial acetic acid, 298.0 g p-dimethylaminobenzaldehyde and 386.0 g of m-dimethylaminobenzoic acid was heated at reflux for a period of approximately four hours. The resulting mixture was cooled to 55° C., diluted with 700 ml of methanol and heated at reflux for approximately thirty minutes. The mixture was then cooled to approximately 15° C. and the solid which separated was collected by filtration and washed with 700.0 ml of fresh methanol chilled to 10°–15° C. The methanolwet solid was reslurried in 400 ml of fresh methanol at 10°–15° C. for approximately twenty minutes, separated by filtration and washed with 150 ml of chilled methanol. The solid was dried at 70° C. in vacuo to yield 453.2 g of 3-(4-dimethylaminophenyl)-6-dimethylaminophthalide (Formula II: R=CH$_3$; X=H; Y=4-(CH$_3$)$_2$N-C$_6$H$_4$ which after recrystallization from toluene was obtained as an ivory-colored solid melting at 184.5°–185.5° C.

Infrared spectral analysis showed a maximum at 1745 (C=O; s) cm$^{-1}$ and the nuclear magnetic resonance spectrum was consistent with the assigned structure.

A toluene solution of this product spotted on an acid clay or an acidic resin develops a green-colored image.

B. A mixture of 6.0 g of 3-(4-dimethylaminophenyl)-6-dimethylaminophthalide prepared as described in part A above, 100 ml of water, 3.5 g of N,N,N′,N′-tetramethyl-m-phenylenediamine and 1.8 g of flake potassium hydroxide was heated at reflux with stirring for a period of approximately eighteen hours and then allowed to cool to room temperature. The resultant solution was made slightly acidic by the addition of ten percent aqueous hydrochloric acid causing a cream-colored solid to precipitate. The solid was collected by filtration, washed with water and air dried at 40° C. to obtain 2-[2,4,4′-tris(dimethylamino)benzhydryl]-5-dimethylaminobenzoic acid (Formula III: R=CH$_3$; X=H; Y=4-(CH$_3$)$_2$NC$_6$H$_4$; Z=2,4-[(CH$_3$)$_2$N]$_2$C$_6$H$_3$) as a slightly sticky, cream-colored solid melting over the range 119°–121° C.

The nuclear magnetic resonance spectrum was in accord with the assigned structure and the infrared spectral analysis had a maximum at 1700 (C=O; b) cm$^{-1}$. Repetition of the above-described procedure but substituting 5.0 g of ammonium hydroxide in one instance and 5.52 g of potassium carbonate in another for the potassium hydroxide also yielded the 2-[2,4,4′-tris(dimethylamino)benzhydryl]-5-dimethylaminobenzoic acid.

C. A solution of 29.78 g of 2-[2,4,4′-tris(dimethylamino)benzhydryl]-5-dimethylaminobenzoic acid prepared as described in part B above, 450.0 g of water and 16.2 g of flake potassium hydroxide was prepared and the pH adjusted to 10.0 by the gradual addition of sodium bicarbonate. The solution was then heated at approximately 75° C. under an atmosphere of oxygen at 60–65 psi for approximately six hours in an agitated stainless steel autoclave. The solid which separated was collected by filtration at ambient temperature, washed with water until alkali free when tested with Brilliant Yellow test paper and dried. The dried solid was slurried with hexane at room temperature, filtered and dried to obtain 23.6 g of 3-(2,4-bis[dimethylamino]-phenyl)-3-(4-dimethylaminophenyl)-6-dimethylaminophthalide (Formula I: R=CH$_3$; X=H; Y=4-(CH$_3$)$_2$NC$_6$H$_4$; Z=2,4-[(CH$_3$)$_2$N]$_2$C$_6$H$_3$) a pale blue-colored solid melting at 171°–172° C.

The nuclear magnetic resonance spectrum was in agreement with the assigned structure and a significant infrared maximum appeared at 1755 (C=O; s) cm$^{-1}$.

A benzene solution of the product spotted on silica gel, an acidic clay or a phenolic resin develops a deep grape-colored image.

EXAMPLE 2

A. A stirred mixture of 35.0 ml of glacial acetic acid, 5.9 g of 3-(4-dimethylaminophenyl)-6-dimethylaminophthalide prepared as in Example 1, part A above, and 3.3 g of 1-ethyl-2-methylindole was heated at reflux for approximately forty-five minutes. After cooling slightly below reflux temperature, 20.0 ml of methanol was added and cooling was continued to ambient temperature. The resulting solution was drowned in 500.0 ml of stirred ice water and, after approximately twenty minutes, the solid which separated was collected by filtration. The solid was slurried at ambient temperature with acetone and the slurry filtered. The collected solid was dried to obtain 4.1 g of 2-[α-(4-dimethylaminophenyl)-α-(1-ethyl-2-methyl-3-indolyl)]methyl-5-dimethylaminobenzoic acid (Formula III: $R=CH_3$; $X=H$; $Y=4-(CH_3)_2NC_6H_4$; $Z=1-C_2H_5-2-CH_3-3$-indolyl) a light tan-colored solid melting at 224°–228° C.

Infrared spectral analysis gave significant maxima at 1685 ($C=O$; s) $cm^{-1}$. The nuclear magnetic resonance spectra was consistent with the assigned structure. Analysis by mass spectrum showed m/e peaks at 455(M+) and 440(M+-CH$_3$).

B. A mixture of 4.0 g of 2-[α-(4-dimethylaminophenyl)-α-(1-ethyl-2-methyl-3-indolyl)]methyl-5-dimethylaminobenzoic acid prepared in part A above, 1.5 g of flake potassium hydroxide and 200.0 ml of water was stirred for approximately seventeen hours at 60°–70° C. under an atmosphere of oxygen. The resulting mixture was cooled to room temperature and the suspended solid was collected by filtration, washed alkali free to Brilliant Yellow test paper with water and dried to obtain 1.5 g of 3-(4-dimethylaminophenyl)-3-(1-ethyl-2-methyl-3-indolyl)-6-dimethylaminophthalide (Formula I: $R=CH_3$; $X=H$; $Y=4-(CH_3)_2NC_6H_4$; $Z=1-C_2H_5-2-CH_3-3$-indolyl) as a light grape-colored solid melting over the range 104°–120° C.

The infrared spectral analysis showed maxima at 1760 ($C=O$; vs) and 1685 ($C=O$; w) $cm^{-1}$.

A toluene solution of this product spotted on silica gel, an acidic clay or a phenolic resin develops a dark grape color.

EXAMPLE 3

A. A stirred mixture of 100 ml of water, 1.8 g of flake potassium hydroxide, 6.0 g of 3-(4-dimethylaminophenyl)-6-dimethylaminophthalide prepared in Example 1, part A above, and 2.90 g of 1,2-dimethylindole was heated at reflux for approximately seventy-five minutes and then set aside at ambient temperature for approximately sixty-four hours. The resulting solution was divided into two equal portions.

One of the portions was chilled by adding ice and slowly made acid by adding acetic acid and dilute hydrochloric acid. A tan-colored resinous solid slowly precipitated from the solution after sufficient sodium acetate was added to saturate the solution. The solid was collected by filtration, washed and air dried at ambient temperature. After recrystallization from denatured ethanol, there was obtained 2-[α-(4-dimethylaminophenyl)-α-(1,2-dimethylindole)]methyl-5-dimethylaminobenzoic acid (Formula III: $R=CH_3$; $X=H$; $Y=4-(CH_3)_2NC_6H_4$; $Z=1,2-(CH_3)_2-3$-indolyl) a cream-colored solid melting over the range 192°–213° C.

The nuclear magnetic resonance spectrum was in accord with the assigned structure and the infrared spectral analysis had a maximum at 1680 ($C=O$; s) $cm^{-1}$.

B. To the second portion of the alkaline aqueous solution from part A, there was added with stirring 75 ml of toluene and 0.7 g of potassium permanganate. The solution gradually changed from green to brown and a small amount of dilute aqueous sodium hydroxide was added to keep the mixture alkaline. The toluene layer was separated and evaporated leaving a tarry residue which was triturated with denatured ethanol to obtain 3-(4-dimethylaminophenyl)-3-(1,2-dimethyl-3-indolyl)-6-dimethylaminophthalide (Formula I: $R=CH_3$; $X=H$; $Y=4-(CH_3)_2NC_6H_4$; $Z=1,2-(CH_3)_2-3$-indolyl) a solid melting at 184°–185° C.

The infrared spectrum had a maximum at 1745 ($C=O$; s) $cm^{-1}$ and the nuclear magnetic resonance spectral analysis was concordant with the assigned structure.

A toluene solution of the product spotted on silica gel, an acidic clay or phenolic resin develops a grape-colored image.

EXAMPLE 4

A. A mixture of 600 ml of water, 10.8 g of flake potassium hydroxide, 36.0 g of 3-(4-dimethylaminophenyl)-6-dimethylaminophthalide prepared as in Example 1, part A above, and 20.0 g of N,N-diethyl-m-toluidine was heated with stirring in a stainless steel autoclave at 120° C. for approximately seven hours and at 160° C. for approximately six hours. The resulting mixture was cooled to ambient temperature and filtered to remove the insolubles. The obtained aqueous solution of the potassium salt of 2-[2-methyl-4,4'-bis(dimethylamino)-benzhydryl]-5-dimethylaminobenzoic acid (Formula III: $R=CH_3$; $X=H$; $Y=4-(CH_3)_2NC_6H_4$; $Z=4-(CH_3)_2N-2-CH_3C_6H_3$) was utilized directly in the oxidation of the next part of this example.

B. The pH of the benzoic acid-potassium salt solution obtained in part A directly above was adjusted to 9.5 by the addition of sodium bicarbonate, the solution was heated at 80° C. for approximately seven hours under an atmosphere of oxygen at 60–65 psi. The resulting mixture was cooled to room temperature; the solid which separated was collected by filtration and dried at room temperature. The solid was dissolved in toluene, treated with decolorizing charcoal and filtered. The toluene solution was extracted with 300 ml of 3N hydrochloric acid and separated. The aqueous acid layer was adjusted to pH 5 by the addition of sodium acetate. The solid which separated was collected by filtration, washed with water and dried in vacuo at 60° C. to obtain 16.5 g of 3-(4-dimethylaminophenyl)-3-(4-diethylamino-2-methylphenyl)-6-dimethylaminophthalide (Formula I: $R=CH_3$; $X=H$; $Y=4-(CH_3)_2-N-C_6H_4$; $Z=4-(C_2H_5)_2N-2-CH_3-C_6H_3$) a solid melting at 183°–184° C.

The nuclear magnetic resonance spectrum was in accord with the assigned structure. Analysis by mass spectrum showed a m/e peak at 457(M+). The infrared spectral analysis had a maximum at 1763 ($C=O$; s) $cm^{-1}$.

A toluene solution of the product spotted on silica gel, an acidic clay or a phenolic resin develops a grape-colored image.

EXAMPLE 5

A. To a stirred mixture of 75.0 ml of monochlorobenzene, 7.4 g of 3-(4-dimethylaminophenyl)-6-dimethylaminophthalide and 2.2 g of N-methylpyrrole maintained at 0°–5° C. by means of an external ice-bath, there was slowly added 6.65 g of anhydrous aluminum chloride. After stirring for approximately three hours, there was slowly added with continued cooling at 0°–5° C., 100 ml of water and 100 ml of ethylene dichloride. The layers were separated and the organic layer extracted with 150 ml of fresh water. The organic layer was then extracted with 100 ml of 3N hydrochloric acid, separated and the pH of this aqueous acid layer adjusted to 4.5 with five percent aqueous sodium hydroxide solution. The green solid which had formed was collected by filtration. After reslurrying in a mixture of acetone and methanol, the solid was filtered and dried to obtain 5.2 g of 2-[α-(4-dimethylaminophenyl)-α-(1-methyl-2-pyrrolyl)]methyl-5-dimethylaminobenzoic acid (Formula III: R=$CH_3$; X=H; Y=4-$(CH_3)_2$—$NC_6H_4$; Z=1-$CH_3$-2-pyrrolyl).

A significant infrared maximum appeared at 1695 (C=O; w) $cm^{-1}$.

B. A mixture of 200 ml of water, 4.8 g of the product from part A directly above and 1.5 g of flake potassium hydroxide was stirred approximately eighteen hours at 60°–70° C. under an atmosphere of oxygen. The solid was collected by filtration, washed with water until alkali free to Brilliant Yellow test paper and dried to obtain 2.0 g of 3-(4-dimethylaminophenyl)-3-(1-methyl-2-pyrrolyl)-6-dimethylaminophthalide (Formula I: R=$CH_3$; X=H; Y=$(CH_3)_2NC_6H_4$; Z=1-$CH_3$-2-pyrrolyl) a gray-colored solid which melted over the range 168°–184° C.

The infrared spectra showed maximum at 1765 (C=O; s) $cm^{-1}$. A toluene solution of the product spotted on silica gel, an acid clay or a phenolic resin develops a purple-colored image.

EXAMPLE 6

A. Following a procedure similar to that described in Example 4, part A above, 36.0 g of 3-(4-dimethylaminophenyl)-6-dimethylaminophthalide prepared as described in Example 1, part A above and 23.0 g of 3-ethoxy-N,N-diethylaniline were interacted to obtain a solution of the potassium salt of 2-[4'-diethylamino-2'-ethoxy-(4-dimethylamino)benzhydryl]-5-dimethylaminobenzoic acid (Formula III: R=$CH_3$; X=H; Y=4-$(CH_3)_2NC_6H_4$; Z=4-$(C_2H_5)_2$N-2-$C_2H_5$O-$C_6H_3$) which was used without isolation in the next step.

B. Proceeding in a manner similar to that described in Example 1, part C above, the potassium salt solution of 2-[4'-diethylamino-2'-ethoxy-(4-dimethylamino)benzhydryl]-5-dimethylaminobenzoic acid from A was oxidized to obtain 6.8 g of 3-(4-diethylamino-2-ethoxyphenyl)-3-(4-dimethylaminophenyl)-6-dimethylaminophthalide (Formula I: R=$CH_3$; X=H; Y=4-$(CH_3)_2NC_6H_4$; Z=4-$(C_2H_5)_2$N-2-$C_2H_5$O-$C_6H_3$) a solid melting over the range 93°–99° C.

The infrared spectral analysis showed a maximum at 1755 (C=O; b, s) $cm^{-1}$. The nuclear magnetic resonance spectrum was in accord with the assigned structure. Mass spectral analysis showed a m/e peak at 487(M+).

A toluene solution of the product spotted on silica gel, an acidic clay or a phenolic resin develops a deep blue-colored image.

EXAMPLE 7

A. Proceeding in a manner similar to that described in Example 4, part A above, 36.0 g of 3-(4-dimethylaminophenyl)-6-dimethylaminophthalide prepared as in Example 1, part A above and 15.0 g of N,N-dimethylaniline were interacted to obtain a solution of the potassium salt of 2-[4,4'-bis(dimethylamino)benzhydryl]-5-dimethylaminobenzoic acid (Formula III: R=$CH_3$; X=H; Y=Z=4-$(CH_3)_2NC_6H_4$) which was used without isolation in the next step.

B. Employing a procedure similar to that described in Example 1, part C above, the potassium salt solution of 2-[4,4'-bis(dimethylamino)benzhydryl]-5-dimethylaminobenzoic acid from A was oxidized to obtain 3,3-bis(4-dimethylaminophenyl)-6-dimethylaminophthalide (Formula I: R=$CH_3$; X=H; Y=Z=4-$(CH_3)_2NC_6H_4$) a tan-colored solid.

A significant infrared maximum appeared at 1750 (C=O; s) $cm^{-1}$. The nuclear magnetic resonance spectra was concordant with the assigned structure.

A toluene solution of the product spotted on silica gel, an acidic clay or a phenolic resin develops a blue-colored image.

EXAMPLE 8

A. Following a procedure similar to that described in Example 1, part A above, 11.6 g of 3-dimethylaminobenzoic acid and 10.6 g of 4-diethylaminobenzaldehyde were interacted to obtain 15.3 g of 3-(4-diethylaminophenyl)-6-dimethylaminophthalide (Formula II: R=$CH_3$; X=H; Y=$(C_2H_5)_2NC_6H_4$) a light brown solid melting in the range 127°–128.5° C.

A significant infrared maximum appeared at 1745 (C=O; s) $cm^{-1}$. Nuclear magnetic resonance analysis was in accord with the assigned structure.

A toluene solution of the product spotted on an acid clay develops a greenish-blue-colored image.

B. Proceeding in a manner similar to that described in Example 1, part B above, 34.4 g of 3-(4-diethylaminophenyl)-6-dimethylaminophthalide prepared as described in part A above and 16.9 g of 1-ethyl-2-methylindole were interacted to obtain the potassium salt of 2-[α-(4-diethylaminophenyl)-α-(1-ethyl-2-methyl-3-indolyl)]methyl-5-dimethylaminobenzoic acid (Formula III: R=$CH_3$; X=H; Y=$(C_2H_5)_2NC_6H_4$; Z=1-$C_2H_5$-2-$CH_3$-3-indolyl) which was not isolated but taken directly into the next step.

C. Employing a procedure similar to that described in Example 1, part C above, for oxidizing the potassium salt of 2-[α-(4-diethylaminophenyl)-α-(1-ethyl-2-methyl-3-indolyl)]methyl-5-dimethylaminobenzoic acid, there was obtained 6.0 g of 3-(4-diethylaminophenyl)-3-(1-ethyl-2-methyl-3-indolyl)-6-dimethylaminophthalide (Formula I: R=$CH_3$; X=H; Y=4-$(CH_3)_2$N—$C_6H_4$; Z=1-$C_2H_5$-2-$CH_3$-3-indolyl) a light purple solid melting at 167°–169° C.

The infrared spectrum had a maximum which appeared at 1752 (C=O; s) $cm^{-1}$. The nuclear magnetic resonance spectrum was in accord with the assigned structure.

A toluene solution of the product spotted on silica gel, an acidic clay or a phenolic resin develops a purple-colored image.

EXAMPLE 9

A. Following a procedure similar to that described in Example 1, part B above, 32.4 g of 3-(diethylamino)phenyl-6-dimethylaminophthalide prepared as described in Example 8, part A above and 16.7 g of N,N,N′,N′-tetramethyl-m-phenylenediamine were interacted to obtain a solution of the potassium salt of 2-[2,4-bis(dimethylamino)-4′-diethylaminobenzhydryl]-5-dimethylaminobenzoic acid (Formula III: $R=CH_3$; $X=H$; $Y=4-(C_2H_5)_2NC_6H_4$; $Z=2,4-[(CH_3)_2N]_2C_6H_3$) which was used without isolation in the next step.

B. Employing a procedure similar to that described in Example 1, part C above, the potassium salt of 2-[2,4-bis(dimethylamino)-4′-diethylaminobenzhydryl]-5-dimethylaminobenzoic acid from A was oxidized to obtain 11.4 g of 3-[2,4-bis(dimethylamino)phenyl]-3-(4-diethylaminophenyl)-6-dimethylaminophthalide (Formula I: $R=CH_3$; $X=H$; $Y=4-(C_2H_5)_2NC_6H_4$; $Z=2,4-[(CH_3)_2N]_2C_6H_3$) as a tan solid melting at 123°–125° C.

A significant infrared maximum appeared at 1758 ($C=O$; s) $cm^{-1}$. The nuclear magnetic resonance spectrum was in agreement with the assigned structure.

A toluene solution of the product spotted on silica gel, an acidic clay or a phenolic resin develops a blackish-purple-colored image.

EXAMPLE 10

A. Employing a procedure similar to that described in Example 1, part A above, for interacting 7.2 g of 4-(N-ethylbenzylamino)benzaldehyde and 5.2 g of 3-dimethylaminobenzoic acid, there was obtained 7.5 g of 3-[4-(N-ethylbenzylamino)phenyl]-6-dimethylaminophthalide (Formula II: $R=CH_3$; $X=H$; $Y=(C_6H_5CH_2)(C_2H_5)NC_6H_4$) as a viscous oil.

The infrared spectral analysis showed a maximum at 1760 ($C=O$; s) $cm^{-1}$. The nuclear magnetic resonance spectrum was consistent with the assigned structure.

A toluene solution of the product spotted on silica gel develops a green-colored image.

B. Following a procedure similar to that described in Example 2, part A above, 4.0 g of 3-[4-(N-ethylbenzylamino)phenyl]-6-dimethylaminophthalide and 1.6 g of 1-ethyl-2-methylindole were interacted to obtain 2-{α-[4-(N-ethylbenzylamino)phenyl]-α-(1-ethyl-2-methyl-3-indolyl)}methyl-5-dimethylaminobenzoic acid (Formula III: $R=CH_3$; $X=H$; $Y=(C_6H_5CH_2(C_2H_5)_2NC_6H_4$; $Z=1-C_2H_5-2-CH_3-3$-indolyl) which was not isolated but used in part D below.

C. Similar results were obtained when the acetic acid reaction medium was replaced with monochlorobenzene and aluminum chloride or trifluoroacetic acid.

D. Proceeding in a manner similar to that described in Example 2, part B above, 2-{α-[4-(N-ethylbenzylamino)phenyl]-α-(1-ethyl-2-methyl-3-indolyl)}methyl-5-dimethylaminobenzoic acid from B above was oxidized to obtain 2.0 g of 3-[4-(N-ethylbenzylamino)phenyl]-3-(1-ethyl-2-methyl-3-indolyl)-6-dimethylaminophthalide (Formula I: $R=CH_3$; $X=H$; $Y=(C_6H_5CH_2)(C_2H_5)NC_6H_4$; $Z=1-C_2H_5-2-CH_3-3$-indolyl) as a pink solid melting over the range 66°–95° C. with decomposition.

Significant infrared maximum appeared at 1760 ($C=O$; s) $cm^{-1}$.

A toluene solution of the product spotted on an acidic resin develops a deep blue-colored image.

EXAMPLE 11

A. Proceeding in a manner similar to Example 1, part A above, 18.3 g of 4-dimethylamino-2-chlorobenzaldehyde and 16.5 g of 3-dimethylaminobenzoic acid were interacted to obtain 20.5 g of 3-(4-dimethylamino-2-chlorophenyl)-6-dimethylaminophthalide (Formula II: $R=CH_3$; $X=H$; $Y=2-Cl-4-(CH_3)_2NC_6H_3$) a red-colored solid melting at 159.5°–160.5° C.

A toluene solution of the product spotted on an acid clay develops a pale green-colored image.

B. Following the procedure described in Example 1, part B above, but substituting triethylamine for potassium hydroxide as the condensing agent, 3-(4-dimethylamino-2-chlorophenyl)-6-dimethylaminophthalide from A is interacted with 5-nitro-1-(4-chlorobenzyl)-2-methylindole to obtain 2-{α-[5-nitro-1-(4-chlorobenzyl)-2-methyl-3-indolyl]-α-(2-chloro-4-dimethylaminophenyl)}methyl-5-dimethylaminobenzoic acid (Formula III: $R=CH_3$; $X=H$; $Y=2-Cl-4-(CH_3)_2NC_6H_3$; $Z=5-NO_2-1-(4-ClC_6H_4CH_2)-2-CH_3-3$-indolyl).

C. Employing a procedure similar to that described in Example 1, part C above, 2-{α-[5-nitro-1-(4-chlorobenzyl)-2-methyl-3-indolyl]-α-(2-chloro-4-dimethylaminophenyl}methyl-5-dimethylaminobenzoic acid from B is oxidized to obtain 3-[5-nitro-1-(4-chlorobenzyl)-2-methyl-3-indolyl]-3-(2-chloro-4-dimethylaminophenyl)-6-dimethylaminophthalide (Formula I: $R=CH_3$; $X=H$; $Y=2-Cl-4-(CH_3)_2NC_6H_3$; $Z=5-NO_2-1-(4-ClC_6H_4CH_2)-2-CH_3-3$-indolyl).

EXAMPLE 12

A. Employing a procedure similar to that described in Example 1, part A above, for interacting 8.2 g of p-anisaldehyde and 11.6 g of 3-dimethylaminobenzoic acid utilizing acetic anhydride alone as the reaction medium there was obtained 9.4 g of 3-(4-methoxyphenyl)-6-dimethylaminophthalide (Formula II: $R=CH_3$; $X=H$; $Y=4-CH_3OC_6H_4$) as a white solid melting at 169°–170° C.

The infrared spectral analysis showed a maximum at 1755 ($C=O$; s) $cm^{-1}$. The nuclear magnetic resonance spectrum was concordant with the assigned structure.

A toluene solution of the product spotted on an acid clay develops a blue-colored image.

B. Proceeding in a manner similar to that described in Example 1, part B above, but substituting lithium carbonate for potassium hydroxide as the condensing agent, 3-(4-methoxyphenyl)-6-dimethylaminophthalide from A is interacted with 1-butyl-2-methylindole to obtain 2-[α-(1-butyl-2-methyl-3-indolyl)-α-(4-methoxyphenyl)]methyl-5-dimethylaminobenzoic acid (Formula III: $R=CH_3$; $X=H$; $Y=4-CH_3OC_6H_4$; $Z=1-C_4H_9-2-CH_3-3$-indolyl).

C. Following the procedure described in Example 1, part C above, 2-[α-(1-butyl-2-methyl-3-indolyl)-α-(4-methoxyphenyl)]methyl-5-dimethylaminobenzoic acid from B is oxidized to obtain 3-(1-butyl-2-methyl-3-indolyl)-3-(4-methoxyphenyl)-6-dimethylaminophthalide (Formula I: $R=CH_3$; $X=H$; $Y=4-CH_3OC_6H_4$; $Z=1-C_4H_9-2-CH_3-3$-indolyl).

D. Employing a procedure similar to that described in Example 1, part B above, 3-(4-methoxyphenyl)-5-dimethylaminophthalide, prepared as described in part A above, was interacted with N,N,N′,N′-tetramethyl-m-phenylenediamine to obtain the potassium salt of 2-[2,4-bis(dimethylamino)-4′-methoxybenzhydryl]-dimethylaminobenzoic acid (Formula III: $R=CH_3$; $X=H$; $Y=4-CH_3OC_6H_4$; $Z=2,4-[(CH_3)_2N]_2C_6H_3$) which was employed in the oxidation step without prior isolation from its alkaline aqueous preparation medium.

E. Proceeding in a manner similar to that described in Example 1, part C above, for oxidizing the potassium salt of 2-[2,4-bis(dimethylamino)-4'-methoxybenzhydryl]-5-dimethylaminobenzoic acid, there was obtained 10.4 g of 3-[2,4-bis(dimethylamino)phenyl]-3-(4-methoxyphenyl)-6-dimethylaminophthalide (Formula I: $R=CH_3$; $X=H$; $Y=4-CH_3OC_6H_4$; $Z=2,4-[(CH_3)_2N]C_6H_3$), an orange-tan-colored solid which melted at 90°-94° C.

The infrared spectrum showed a maximum at 1762 ($C=O$; s) cm$^{-1}$. The nuclear magnetic resonance spectrum was consistent with the assigned structure.

A toluene solution of the product spotted on phenolic resin develops a black-colored image.

EXAMPLE 13

A. Proceeding in a manner similar to Example 1, part A above, 11.6 g of 3-dimethylaminobenzoic acid and 8.2 g of o-anisaldehyde were interacted using acetic anhydride alone as the reaction medium to obtain 11.7 g of 3-(2-methoxyphenyl)-6-dimethylaminophthalide (Formula II: $R=CH_3$; $X=H$; $Y=2-CH_3OC_6H_4$) as an orange solid melting at 165°-166.5° C.

A significant infrared maximum appeared at 1760 ($C=O$; s) cm$^{-1}$. The nuclear magnetic resonance spectra was concordant with the assigned structure.

A toluene solution of the product spotted on an acid clay develops a pale yellow-colored image.

B. Following the procedure described in Example 1, part B above, 3-(2-methoxyphenyl)-6-dimethylaminophthalide from A is interacted with N,N,N',N'-tetrabutyl-m-phenylenediamine to obtain 2-[2,4-bis(dibutylamino)-(2'-methoxy)benzhydryl]-5-dimethylaminobenzoic acid (Formula III: $R=CH_3$; $X=H$; $Y=2-CH_3OC_6H_4$; $Z=2,4-[(C_4H_9)_2N]_2C_6H_3$).

C. Employing a procedure similar to that described in Example 1, part C above, 2-[2,4-bis(dibutylamino)-(2'-methoxyphenyl)benzhydryl]-5-dimethylaminobenzoic acid from B is oxidized to obtain 3-[2,4-bis(dibutylamino)phenyl]-3-(2-methoxyphenyl)-6-dimethylaminophthalide (Formula I: $R=CH_3$; $X=H$; $Y=2-CH_3OC_6H_4$; $Z=2,4-[(C_4H_9)_2N]_2C_6H_3$).

EXAMPLE 14

A. Following a procedure similar to that described in Example 1, part A above, 11.6 g of 3-dimethylaminobenzoic acid and 9.0 g of 4-ethoxybenzaldehyde were interacted in acetic anhydride to obtain 2.6 g of 3-(4-ethoxyphenyl)-6-dimethylaminophthalide (Formula II: $R=CH_3$; $Y=H$; $Y=4-C_2H_5OC_6H_4$) as a white solid melting at 115.5°-118° C.

Infrared spectral analysis showed a maximum at 1750 ($C=O$; s) cm$^{-1}$. The nuclear magnetic resonance analysis was in accord with the assigned structure.

A toluene solution of the product spotted on an acid clay develops a green-colored image.

B. Employing a procedure similar to that described in Example 1, part B above, 3-(4-ethoxyphenyl)-6-dimethylaminophthalide from A is interacted with N,N-dimethyl-m-toludine to obtain 2-(4-dimethylamino-2-methyl-4'-ethoxybenzhydryl)-5-dimethylaminobenzoic acid (Formula III: $R=CH_3$; $X=H$; $Y=4-C_2H_5OC_6H_4$; $Z=4-(CH_3)_2N-2-CH_3-C_6H_3$).

C. Proceeding in a manner similar to that described in Example 1, part C above, 2-(4-dimethylamino-2-methyl-4'-ethoxybenzhydryl)-5-dimethylaminobenzoic acid from part B above is oxidized to obtain 3-(4-dimethylamino-2-methylphenyl)-3-(4-ethoxyphenyl)-6-dimethylaminophthalide (Formula I: $R=CH_3$; $X=H$; $Y=C_2H_5OC_6H_4$; $Z=4-(CH_3)_2N-2-CH_3C_6H_3$).

EXAMPLE 15

A. Employing a procedure similar to that described in Example 1, part A above, for interacting 11.6 g of 3-dimethylaminobenzoic acid and 10.6 g of 3,4-dimethoxybenzaldehyde in acetic anhydride there was obtained 0.75 g of 3-(3,4-dimethoxyphenyl)-6-dimethylaminophthalide (Formula II: $R=CH_3$; $X=H$; $Y=3,4-(CH_3O)_2C_6H_3$) a light yellow-colored solid melting at 148°-150° C.

A significant infrared maximum appeared at 1765 ($C=O$; s) cm$^{-1}$.

A toluene solution of the product spotted on an acid clay develops a pale yellow-colored image.

B. Proceeding in a manner similar to that described in Example 1, part B above, but substituting quinuclidine for potassium hydroxide as the condensing agent, 3-(3,4-dimethoxyphenyl)-6-dimethylaminophthalide from A is interacted with 1-octyl-2-methylindole to obtain 2-[α-(1-octyl-2-methyl-3-indolyl)-α-(3,4-dimethoxyphenyl)]methyl-5-dimethylaminobenzoic acid (Formula III: $R=CH_3$; $X=H$; $Y=3,4-(CH_3O)_2C_6H_3$; $Z=1-C_8H_{17}-2-CH_3$-indolyl).

C. Following the procedure described in Example 2, part B above, 2-[α-(1-octyl-2-methyl-3-indolyl)-α-(3,4-dimethoxyphenyl)]methyl-5-dimethylaminobenzoic acid from B is oxidized to obtain 3-(1-octyl-2-methyl-3-indolyl)-3-(3,4-dimethoxyphenyl)-6-dimethylaminophthalide (Formula I: $R=CH_3$; $X=H$; $Y=3,4-(CH_3O)_2C_6H_3$; $Z=1-C_8H_{17}-2-CH_3-3$-indolyl).

EXAMPLE 16

A. Proceeding in a manner similar to Example 1, part A above, 14.35 g of 4-diethylamino-2-methylbenzaldehyde and 12.37 g of 3-dimethylaminobenzoic acid were interacted in acetic anhydride to obtain 5.3 g of 3-(4-diethylamino-2-methylphenyl)-6-dimethylaminophthalide (Formula II: $R=CH_3$; $X=H$; $Y=4-(C_2H_5)_2N-2-CH_3C_6H_3$) a solid melting at 135°-136.5° C.

The infrared spectral analysis showed a maximum at 1750 ($C=O$; s) cm$^{-1}$. The nuclear magnetic resonance spectra was in accord with the assigned structure.

A toluene solution of the product spotted on an acid clay develops a bluish-green-colored image.

B. Following the procedure described in Example 1, part B above, but substituting lithium hydroxide for potassium hydroxide as the condensing agent, 3-(4-diethylamino-2-methylphenyl)-6-dimethylaminophthalide from A is interacted with 1-(2,5-dimethylbenzyl)-2-methylindole to obtain 2-{α-[1-(2,5-dimethylbenzyl)-2-methyl-3-indolyl]-α-(4-diethylamino-2-methylphenyl)} methyl-5-dimethylaminobenzoic acid (Formula III: $R=CH_3$; $X=H$; $Y=4-(C_2H_5)_2N-2-CH_3C_6H_3$; $Z=1-[2,5-(CH_3)_2C_6H_3CH_2]-2-CH_3-3$-indolyl).

EXAMPLE 17

A. Employing a procedure similar to that described in Example 1, part A above, for interacting 11.6 g of 3-dimethylaminobenzoic acid and 12.4 g of 89 percent 3-ethoxy-4-methoxybenzaldehyde in acetic anhydride, there was obtained 3-(3-ethoxy-4-methoxyphenyl)-6-dimethylaminophthalide (Formula II: $R=CH_3$; $X=H$; $Y=3-C_2H_5O-4-CH_3O-C_6H_3$) a solid which had an infrared spectrum maximum at 1760 ($C=O$; s) cm$^{-1}$.

B. Proceeding in a manner similar to that described in Example 1, part B above, 3-(3-ethoxy-4-methoxyphenyl)-6-dimethylaminophthalide from A is interacted with N,N,N',N'-tetrasec-butyl-m-phenylenediamine to obtain 2-[2,4-bis(di-sec-butylamino)-3'-ethoxy-4'-methoxybenzhydryl]-5-dimethylaminobenzoic acid (Formula III: $R=CH_3$; $X=H$; $Y=3-C_2H_5O-4-CH_3OC_6H_3$; $Z=2,4-[(s-C_4H_9)_2N]_2C_6H_3$).

C. Following the procedure described in Example 1, part C above, 2-[2,4-bis(di-sec-butylamino)-3'-ethoxy-4'-methoxybenzhydryl]-5-dimethylaminobenzoic acid from B is oxidized to obtain 3-[2,4-bis(di-sec-butylamino)phenyl]-3-(3-ethoxy-4-methoxyphenyl)-6-dimethylaminophthalide (Formula I: $R=CH_3$; $X=H$; $Y=3-C_2H_5O-4-CH_3OC_6H_3$; $Z=2,4-[(s-C_4H_9)_2N]_2C_6H_3$).

EXAMPLE 18

A. Proceeding in a manner similar to Example 1, part A above, 11.6 g of 3-dimethylaminobenzoic acid and 10.0 g of 2,4-dimethoxybenzaldehyde were interacted in acetic anhydride to obtain 14.0 g of 2-(2,4-dimethoxyphenyl)-6-dimethylaminophthalide (Formula II: $R=CH_3$; $X=H$; $Y=2,4-(CH_3O)_2C_6H_3$) as a yellow-colored solid melting at 123°–125° C.

A significant infrared maximum appeared at 1750 ($C=O$; s) cm$^{-1}$.

A toluene solution of the product spotted on an acid clay develops a blue-colored image.

B. Following the procedure described in Example 1, part B above, but substituting tetraethylammonium hydroxide for potassium hydroxide as the condensing agent, 3-(2,4-dimethoxyphenyl)-6-dimethylaminophthalide from A is interacted with 5-iodo-1-(1-methylhexyl)indole to obtain 2-{α-[5-iodo-1-(1-methylhexyl)-3-indolyl]-α-(2,4-dimethoxyphenyl)}methyl-5-dimethylaminobenzoic acid (Formula III: $R=CH_3$; $X=H$; $Y=2,4-(CH_3O)_2C_6H_3$; $Z=5-I-1-[1-CH_3(C_6H_{12})]-3$-indolyl).

C. Employing a procedure similar to that described in Example 2, part B above, 2-{α-[5-iodo-1-(1-methylhexyl)-3-indolyl]-α-(2,4-dimethoxyphenyl)}methyl-5-dimethylaminobenzoic acid from B is oxidized to obtain 3-[5-iodo-1-(1-methylhexyl)-3-indolyl]-3-(2,4-dimethoxyphenyl)-6-dimethylaminophthalide (Formula I: $R=CH_3$; $X=H$; $Y=2,4-(CH_3O)_2C_6H_3$; $Z=5-I-1-[1-CH_3-(C_6H_{12})]-3$-indolyl).

D. Proceeding in a manner similar to that described in Example 1, part B above, 25.1 g of 3-(2,4-dimethoxyphenyl)-6-dimethylaminophthalide prepared as described in part A above and 13.4 g of N,N,N',N'-tetramethyl-m-phenylenediamine were interacted to obtain the potassium salt of 2-[2,4-dimethoxy-2',4'-bis(dimethylamino)benzhydryl]-5-dimethylaminobenzoic acid (Formula III: $R=CH_3$; $X=H$; $Y=2,4-(CH_3O)_2C_6H_3$; $Z=2,4-[(CH_3)_2N]_2C_6H_3$) which was employed in the oxidation step without prior isolation from its aqueous preparation medium.

E. Following the procedure described in Example 1, part C above, for oxidizing the potassium salt of 2-[2,4-dimethoxy-2',4'-bis(dimethylamino)benzhydryl]-5-dimethylaminobenzoic acid, there was obtained 9.0 g of 3-(2,4-dimethoxyphenyl)-3-[2,4-bis(dimethylamino)phenyl]-6-dimethylaminophthalide (Formula I: $R=CH_3$; $X=H$; $Y=2,4-(CH_3O)_2C_6H_3$; $Z=2,4-[(CH_3)_2N]_2C_6H_3$) a reddish-brown-colored solid which melted over the range 153°–160° C.

A significant infrared maximum appeared at 1760 ($C=O$; s) cm$^{-1}$. The nuclear magnetic resonance spectrum was consistent with the assigned structure.

A toluene solution of the product spotted on a phenolic resin develops a reddish-brown-colored image.

F. Employing a procedure similar to that described in Example 1, part B above, 25.1 g of 3-(2,4-dimethoxyphenyl)-6-dimethylaminophthalide prepared as described in part A above, and 15.5 g of 1-ethyl-2-methylindole were interacted to obtain the potassium salt of 2-[α-(2,4-dimethoxyphenyl)-α-(1-ethyl-2-methyl-3-indolyl)]methyl-5-dimethylaminobenzoic acid (Formula III: $R=CH_3$; $X=H$; $Y=2,4-(CH_3O)_2C_6H_3$; $Z=1-C_2H_5-2-CH_3-3$-indolyl) which was used in the oxidation step without prior isolation from its aqueous preparation medium.

G. Proceeding in a manner similar to that described in Example 1, part C above, for oxidizing the potassium salt of 2-[α-(2,4-dimethoxyphenyl)-α-(1-ethyl-2-methyl-3-indolyl)]methyl-5-dimethylaminobenzoic acid, there was obtained 1.6 g of 3-(2,4-dimethoxyphenyl)-3-(1-ethyl-2-methyl-3-indolyl)-6-dimethylaminophthalide (Formula I: $R=CH_3$; $X=H$; $Y=2,4-(CH_3O)_2-C_6H_3$; $Z=1-C_2H_5-2-CH_3-3$-indolyl) an off-white solid which melted at 215°–217° C.

A significant infrared maximum appeared at 1764 ($C=O$; s) cm$^{-1}$. The nuclear magnetic resonance spectrum was in accord with the assigned structure.

A toluene solution of the product spotted on silica gel develops a grape-colored image.

EXAMPLE 19

A. Following a procedure similar to that described in Example 1, part A above, 7.8 g of 3-dimethylaminobenzoic acid and 8.9 g of 9-ethyl-3-carbazolcarboxaldehyde were interacted in acetic anhydride to obtain 6.33 g of 3-(9-ethyl-3-carbazolyl)-6-dimethylaminophthalide (Formula II: $R=CH_3$; $X=H$; $Y=9-C_2H_5-3$-carbazolyl) as a light brown solid melting over the range 142°–145° C.

A significant infrared maximum appeared at 1760 ($C=O$; s) cm$^{-1}$.

A toluene solution of the product spotted on an acid clay develops a greenish-blue-colored image.

B. Employing a procedure similar to that described in Example 1, part B above, 3-(9-ethyl-3-carbazolyl)-6-dimethylaminophthalide from A is interacted with N,N,N',N'-tetrabutyl-m-phenylenediamine to obtain 2-[α-(9-ethyl-3-carbazolyl)]-α-[2,4-bis(dibutylamino)phenyl]methyl-5-dimethylaminobenzoic acid (Formula III: $R=CH_3$; $X=H$; $Y=9-C_2H_5-3$-carbazolyl; $Z=2,4-[(C_4H_9)_2N]_2C_6H_3$).

C. Proceeding in a manner similar to that described in Example 1, part C above, 2-[α-(9-ethyl-3-carbazolyl)]-α-[2,4-bis(dibutylamino)phenyl]methyl-5-dimethylaminobenzoic acid from B is oxidized to obtain 3-(9-ethyl-3-carbazolyl)-3-[2,4-bis(dibutylamino)phenyl]-6-dimethylaminophthalide (Formula I: $R=CH_3$; $X=H$; $Y=9-C_2H_5-3$-carbazolyl; $Z=2,4-[(C_4H_9)_2N]_2C_6H_3$).

EXAMPLE 20

A. Proceeding in a manner similar to Example 1, part A above, 5.0 g of 9-formyljulolidine and 4.6 g of 3-dimethylaminobenzoic acid were interacted to obtain 5.0 g of 3-(9-julolidinyl)-6-dimethylaminophthalide (Formula II: $R=CH_3$; $X=H$; $Y=9$-julolidinyl).

In the infrared spectral analysis, a maximum was observed at 1760 ($C=O$; s) cm$^{-1}$.

A toluene solution of the product spotted on an acid clay develops a green-colored image.

B. Following the procedure described in Example 1, part B above, but substituting sodium carbonate for potassium hydroxide as the condensing agent, 3-(9-julolidinyl)-6-dimethylaminophthalide from A is interacted with 5-methoxy-1-butylindole to obtain 2-[α-(5-methoxyl-1-butyl-3-indolyl)-α-(9-julolidinyl)]methyl-5-dimethylaminobenzoic acid (Formula III: R=CH$_3$; X=H; Y=9-julolidinyl; Z=5-CH$_3$O-1-C$_4$H$_9$-3-indolyl).

EXAMPLE 21

A. Following a procedure similar to that described in Example 1, part A above, 7.5 g of 3,4-(methylenedioxy)-benzaldehyde and 9.1 g of 3-dimethylaminobenzoic acid were interacted in acetic anhydride to obtain 0.9 g of 3-(3,4-methylenedioxyphenyl)-6-dimethylaminophthalide (Formula II: R=CH$_3$; X=H; Y=1-[3,4-(OCH$_2$O)C$_6$H$_3$]) a light yellow solid melting over the range 134°–143° C.

A significant infrared maximum appeared at 1750 (C=O; s) cm$^{-1}$. The nuclear magnetic resonance spectra was concordant with the assigned structure. Analysis by mass spectrum showed a m/e peak at 297(M+).

A toluene solution of the product spotted on an acid clay develops a green-colored image.

B. Employing a procedure similar to that described in Example 1, part B above, but substituting ammonium hydroxide for potassium hydroxide as the condensing agent, 3-(3,4-methylenedioxyphenyl)-6-dimethylaminophthalide from A is interacted with 2-isopropylindole to obtain 2-[α-(2-isopropyl-3-indolyl)-α-(3,4-methylenedioxyphenyl)]methyl-5-dimethylaminobenzoic acid (Formula III: R=CH$_3$; X=H; Y=1-[3,4(OCH$_2$O)C$_6$H$_3$]; Z=2-i-C$_3$H$_7$-3-indolyl).

C. Proceeding in a manner similar to that described in Example 1, part C above, 2-[α-(2-isopropyl-3-indolyl)-α-(3,4-methylenedioxyphenyl)]methyl-5-dimethylaminobenzoic acid from B is oxidized to obtain 3-(2-isopropyl-3-indolyl)-3-(3,4-methylenedioxyphenyl)-6-dimethylaminophthalide (Formula I: R=CH$_3$; X=H; Y=1-[3,4(OCH$_2$O)C$_6$H$_3$]; Z=2-i-C$_3$H$_7$-3-indolyl).

EXAMPLE 22

A. Proceeding in a manner similar to Example 1, part A above, 5.6 g of 2-thiophenecarboxaldehyde and 9.1 g of 3-dimethylaminobenzoic acid were interacted in acetic anhydride to obtain 0.92 g of 3-(2-thienyl)-6-dimethylaminophthalide (Formula II: R=CH$_3$; X=H; Y=2-thienyl) as an oily white-colored solid.

The infrared spectral analysis showed a maximum at 1763 (C=O; s) cm$^{-1}$. The nuclear magnetic resonance spectrum was concordant with the assigned structure.

A toluene solution of the product spotted on an acid clay develops a yellow-colored image.

B. Following the procedure described in Example 1, part B above, 3-(2-thienyl)-6-dimethylaminophthalide from A is interacted with N,N,N',N'-tetraethyl-m-phenylenediamine to obtain 2-{α-(2-thienyl)-α-[2,4-bis(-diethylamino)phenyl]methyl-5-dimethylaminobenzoic acid (Formula III: R=CH$_3$; X=H; Y=2-thienyl; Z=2,4-[(C$_2$H$_5$)$_2$N]$_2$C$_6$H$_3$).

C. Employing a procedure similar to that described in Example 1, part C above, 2-{α-(2-thienyl)-α-[2,4-bis(-diethylamino)phenyl}methyl-5-dimethylaminobenzoic acid from B is oxidized to obtain 3-(2-thienyl)-3-[2,4-bis(diethylamino)phenyl]-6-dimethylaminophthalide (Formula I; R=CH$_3$; X=H; Y=2-thienyl; Z=2,4-[(C$_2$H$_5$)$_2$N]$_2$C$_6$H$_3$).

EXAMPLE 23

A. Following a procedure similar to that described in Example 1, part A above, 7.7 g of 3-dimethylaminobenzoic acid and 4.4 g of N-methylpyrrole-2-carboxaldehyde were interacted in acetic anhydride to obtain 3-(1-methyl-2-pyrrolyl)-6-dimethylaminophthalide (Formula II: R=CH$_3$; X=H; Y=1-CH$_3$-2-pyrrolyl).

The significant infrared maximum appeared at 1760 (C=O; s) cm$^{-1}$.

A toluene solution of the product spotted on an acid clay develops a purple-colored image.

B. Employing a procedure similar to that described in Example 2, part A above, 3-(1-methyl-2-pyrrolyl)-6-dimethylaminophthalide from A is interacted with 1-vinyl-2-methylindole to obtain 2-[α-(1-vinyl-2-methyl-3-indolyl)-α-(1-methyl-2-pyrrolyl)]methyl-5-dimethylaminobenzoic acid (Formula III: R=CH$_3$; X=H; Y=1-CH$_3$-2-pyrrolyl; Z=1-CH$_2$=CH-2-CH$_3$-3-indolyl).

C. Proceeding in a manner similar to that described in Example 1, part C above, 2-[α-(1-vinyl-2-methyl-3-indolyl)-α-(1-methyl-2-pyrrolyl)]methyl-5-dimethylaminobenzoic acid from part B above is oxidized to obtain 3-(1-vinyl-2-methyl-3-indolyl)-3-(1-methyl-2-pyrrolyl)-6-dimethylaminophthalide (Formula I: R=CH$_3$; X=H; Y=1-CH$_3$-2-pyrrolyl; Z=1-CH$_2$=CH-2-CH$_3$-3-indolyl).

EXAMPLE 24

A. Employing a procedure similar to that described in Example 1, part A above, for interacting 4.6 g of 3-dimethylaminobenzoic acid and 4.6 g of 1-ethyl-2-methylindole-3-carboxaldehyde in acetic anhydride to obtain 2.6 g of 3-(1-ethyl-2-methyl-3-indolyl)-6-dimethylaminophthalide (Formula II: R=CH$_3$; X=H; Y=1-C$_2$H$_5$-2-CH$_3$-3-indolyl) a light brown solid melting at 177°–180° C.

A significant infrared maximum appeared at 1747 (C=O; s) cm$^{-1}$. The nuclear magnetic resonance spectrum was in accord with the assigned structure.

A toluene solution of the product spotted on an acid clay develops a purple-colored image.

B. Proceeding in a manner similar to that described in Example 5, part A above, 3-(1-ethyl-2-methyl-3-indolyl)-6-dimethylaminophthalide from A is interacted with 1-ethyl-2-methylindole to obtain 2-[α,α-bis(1-ethyl-2-methyl-3-indolyl)]methyl-5-dimethylaminobenzoic acid (Formula III: R=CH$_3$; X=H; Y=Z=1-C$_2$H$_5$-2-CH$_3$-3-indolyl).

EXAMPLE 25

A. Following a procedure similar to that described in Example 1, part A above, 1,2-dimethylindole-3-carboxaldehyde and 3-dimethylaminobenzoic acid are interacted to form 3-(1,2-dimethyl-3-indolyl)-6-dimethylaminophthalide (Formula II: R=CH$_3$; X=H; Y=1,2-(CH$_3$)$_2$-3-indolyl) which melts at 234°–236° C.

B. Employing a procedure similar to that described in Example 1, part B above, 3-(1,2-dimethyl-3-indolyl)-6-dimethylaminophthalide from A is interacted with N,N,N',N'-tetraethyl-m-phenylenediamine to obtain 2-{α-(1,2-dimethyl-3-indolyl)-α-[2,4-bis(dimethylamino)]phenyl}methyl-5-dimethylaminobenzoic acid (Formula III: R=CH$_3$; X=H; Y=1,2-(CH$_3$)$_2$-3-indolyl; Z=2,4-bis[(CH$_3$)$_2$N]$_2$C$_6$H$_3$).

EXAMPLE 26

A. A stirred mixture of 98.0 ml of N,N-dimethylaniline and 20.9 g of 3-(4-dimethylaminophenyl)-6-dimethylaminophthalide prepared as in Example 1, part A above, was warmed to approximately 75° C. to form a clear solution which was then cooled by means of a cold water bath to 20° C. Over a period of ten minutes, 9.5 g of anhydrous zinc chloride was slowly added to the solution while allowing the temperature to rise to approximately 24° C. After stirring for approximately thirty minutes at a temperature in the range of 25° to 30° C., the reaction mixture was heated to approximately 50° C. and maintained in the range of 50°–55° C. for two hours during which time two charges of 1.9 g each of anhydrous zinc chloride were added to the reaction mixture. Then 150.0 ml of hot tap water and 20 g of 50 percent aqueous sodium hydroxide were slowly added and the resulting mixture was set aside at ambient temperature overnight. The excess N,N-dimethylaniline was steam-distilled from the reaction mixture. After cooling to approximately 75° C., diatomaceous earth was added, the resultant mixture filtered and the filter cake washed with 40.0 ml of warm water. The wash was combined with the alkaline filtrate and the whole solution slowly dripped into a mixture of 35.0 ml of water and 18.0 ml of acetic acid with vigorous stirring. The pH of the resulting slurry was adjusted to 4.9 by the addition of ten percent aqueous sodium hydroxide. After cooling to 25° C. the light blue solid was collected by filtration, washed with water and dried in vacuo to obtain 25.0 g of 2-[4,4'-bis(dimethylamino)-benzhydryl]-5-dimethylaminobenzoic acid (Formula III: R=CH$_3$; X=H; Y=Z=4-(CH$_3$)$_2$NC$_6$H$_4$) a light gray solid which melted at 208°–211° C.

The infrared spectral analysis showed a maximum at 1655 (C=O; s) cm$^{-1}$.

B. Employing a procedure similar to that described in Example 1, part C above, 2-[4,4'-bis(dimethylamino)-benzhydryl]-5-dimethylaminobenzoic acid prepared as described in part A above was oxidized to obtain 3,3-bis(4-dimethylaminophenyl)-6-dimethylaminophthalide (Formula I: R=CH$_3$; X=H; Y=Z=4-(CH$_3$)$_2$NC$_6$H$_4$), a tan-colored solid which melted at 173.5°–178.5° C.

A significant infrared maximum appeared at 1750 (C=O; s) cm$^{-1}$. The nuclear magnetic resonance spectrum was consistent with the assigned structure.

A toluene solution of the product spotted on silica gel, an acidic clay or a phenolic resin develops a blue-colored image.

C. Following a procedure similar to that described in part A above, but substituting 18.2 g of anhydrous stannic chloride for the anhydrous zinc chloride, 70.0 ml of N,N-dimethylaniline and 14.9 g of 3-(4-dimethylaminophenyl)-6-dimethylaminophthalide prepared as described in Example 1, part A above were interacted to obtain 15.0 g of 2-[4,4'-bis(dimethylamino)-benzhydryl]-5-dimethylaminobenzoic acid which melted at 208°–212° C.

A significant infrared maximum appeared at 1705 (C=O; s) cm$^{-1}$.

D. Proceeding in a manner similar to that described in part A above, but replacing the anhydrous zinc chloride with 9.3 g of anhydrous aluminum chloride, 70.0 ml of N,N-dimethylaniline and 14.9 g of 3-(4-dimethylaminophenyl)-6-dimethylaminophthalide, prepared as described in Example 1, part A above were interacted to obtain 16.1 g of 2-[4,4'-bis(dimethylamino)-benzhydryl]-5-dimethylaminobenzoic acid, a light blue powder which melted at 209°–213° C.

A significant infrared maximum appeared at 1705 (C=O; s) cm$^{-1}$. The nuclear magnetic resonance spectrum is consistent with the assigned structure.

E. Following the procedure described in part A directly above, 70.0 ml of N,N-dimethylaniline and 14.9 g of 3-(4-dimethylaminophenyl)-6-dimethylaminophthalide were interacted in the presence of 15.0 g of anhydrous ferric chloride. The reaction mixture was drowned in water and subjected to steam-distillation to remove the excess N,N-dimethylaniline. Then there was added to the remaining aqueous mixture 120.0 ml of toluene, 25.0 ml of water and diatomaceous earth. The resulting mixture was stirred at 75°–80° C., filtered and the filter cake washed twice with 25.0 ml portions of hot toluene. The washes were combined with the filtrate, the aqueous layer separated and cooled to approximately 40° C. The pH was adjusted to 4.9 by the addition of acetic acid. The solid that formed was collected by filtration, washed with water and dried to obtain 0.2 g of somewhat impure 2-[4,4'-bis(dimethylamino)benzhydryl]-5-dimethylaminobenzoic acid (Formula III: R=CH$_3$; X=H; Y=Z=4-(CH$_3$)$_2$C$_6$H$_4$), a pale blue-colored solid which melted at 187.5°–193° C.

A significant infrared maximum appeared at 1710 (C=O; s) cm$^{-1}$.

The remaining toluene layer from above was evaporated to dryness to obtain 26.0 g of a sticky pale blue-colored solid. A ten gram aliquot of the solid was slurried in 50.0 ml of hot toluene, the undissolved solid collected by filtration after cooling to room temperature and washed with 10.0 ml of toluene and dried in vacuo to obtain 5.8 g of an iron complex of 2-[4,4'-bis(-dimethylamino)benzhydryl]-5-dimethylaminobenzoic acid as a gray-colored solid. The thus obtained iron complex was slurried in water and rendered alkaline to phenolphthalein test paper by the addition of five percent aqueous sodium hydroxide, heated to approximately 90° C., cooled to approximately 30° C. and filtered twice through diatomaceous earth. The slightly hazy filtrate was slowly made acid to approximately pH 5 by the addition of dilute aqueous acetic acid. The solid which separated was collected by filtration, washed with water and air dried to obtain 2-[4,4'-bis(dimethylamino)benzhydryl]-5-dimethylaminobenzoic acid (Formula III: R=CH$_3$; X=H; Y=Z=4-(CH$_3$)$_2$NC$_6$H$_4$) as a light gray-colored solid which melted over the range 203°–210° C.

The infrared spectrum had a significant maximum at 1710 (C=O; s) cm$^{-1}$. The nuclear magnetic resonance spectrum was concordant with the assigned structure.

The combined toluene filtrate and wash from above was evaporated to obtain 4.4 g of 3,3-bis(4-dimethylaminophenyl)-6-dimethylaminophthalide (Formula I: R=CH$_3$; X=H; Y=Z=4-(CH$_3$)$_2$NC$_6$H$_4$), a dark blue-colored solid.

A significant infrared maximum appeared at 1759 (C=O; s) cm$^{-1}$. The nuclear magnetic resonance spectrum was consistent with the assigned structure.

A toluene solution of the product spotted on silica gel develops a blue-colored image.

F. Proceeding in a manner similar to that described in part E above, 0.3 g of 3-(2,4-dimethoxyphenyl)-6-dimethylaminophthalide, prepared in a manner similar to Example 18, part A above, was interacted with 3.0 ml of N,N-dimethylaniline in the presence of 0.3 g of anhydrous ferric chloride to obtain significant amounts of 2-[(2,4-dimethoxy-4'-dimethylamino-benzhydryl]-5-dimethylaminobenzoic acid (Formula III: $R=CH_3$; $X=H$; $Y=2,4-(CH_3O)_2C_6H_3$; $Z=4-(CH_3)_2NC_6H_4$) and 3-(4-dimethylaminophenyl)-3-(2,4-dimethoxyphenyl)-6-dimethylaminophthalide (Formula I: $R=CH_3$; $X=H$; $Y=2,4-(CH_3O)_2C_6H_3$; $Z=4-(CH_3)_2NC_6H_4$).

G. Employing a procedure similar to that described in part E above, 0.3 g of 3-(4-dimethylaminophenyl)-6-dimethylaminophthalide prepared as described in Example 1, part A above was interacted with 3.0 ml of 1-ethyl-2-methylindole in the presence of 0.32 g of anhydrous ferric chloride to obtain significant amounts of 2-[α-(4-dimethylaminophenyl)-α-(1-ethyl-2-methyl-3-indolyl)]methyl-5-dimethylaminobenzoic acid (Formula III: $R=CH_3$; $X=H$; $Y=4-(CH_3)_2NC_6H_4$; $Z=1-C_2H_5-2-CH_3-3$-indolyl) and 3-(4-dimethylaminophenyl)-3-(1-ethyl-2-methyl-3-indolyl)-6-dimethylaminophthalide (Formula I: $R=CH_3$; $X=H$; $Y=4-(CH_3)_2NC_6H_4$; $Z=1-C_2H_5-2-CH_3-3$-indolyl).

EXAMPLE 27

A. Following the procedure described in Example 26, part A, 9.9 g of 3-(4-methoxyphenyl)-6-dimethylaminophthalide, prepared as described in Example 12, part A above, and 89.0 ml of N,N-dimethylaniline were interacted in the presence of 9.5 g of anhydrous zinc chloride at room temperature to obtain 13.7 g of 2-(4-dimethylamino-4'-methoxybenzhydryl)-5-dimethylaminobenzoic acid as an off-white colored solid melting at 185°-190° C.

B. A stirred mixture of 8.1 g of 2-(4-dimethylamino-4'-methoxybenzhydryl)-5-dimethylaminobenzoic acid from part A above, 40.0 ml of water, 1.6 g of 50 percent aqueous sodium hydroxide and 2.7 ml of isopropyl alcohol was maintained at a temperature in the range of 85°-96° C. while 20.3 g of ten percent aqueous hydrogen peroxide was added over a period of approximately six hours. The reaction mixture was set aside at ambient temperature overnight. The solid was collected by filtration, washed free of alkali with water and dried in vacuo to obtain 5.5 g of 3-(4-dimethylaminophenyl)-3-(4-methoxyphenyl)-6-dimethylaminophthalide, a yellow-colored solid which melted at 156°-161° C.

A significant infrared maximum appeared at 1754 ($C=O$; s) cm$^{-1}$. The nuclear magnetic resonance spectrum was consistent with the assigned structure.

A toluene solution of the product spotted on an acid clay or an acidic resin develops a green-colored image.

EXAMPLE 28

A. Proceeding in a manner similar to that described in Example 26, part A above, 10.7 g of 3-(4-dimethylaminophenyl)-6-dimethylaminophthalide, prepared as described in Example 1, part A above and 50.0 ml of N-methylaniline were interacted in the presence of anhydrous zinc chloride at room temperature to obtain 13.8 g of 2-[(4-dimethylamino-4'-methylamino)benzhydryl]-5-dimethylaminobenzoic acid (Formula III: $R=CH_3$; $X=H$; $Y=4-(CH_3)_2-NC_6H_4$; $Z=4-CH_3NHC_6H_4$) as a tan-colored solid softening at 118° C. and melting at 128°-130° C.

A significant infrared maximum appeared at 1691 ($C=O$; s) cm$^{-1}$. The nuclear magnetic resonance spectrum was in accord with the assigned structure.

B. Following a procedure similar to that described in Example 27, part B above, 6.0 g of 2-[(4-dimethylamino-4'-methylamino)benzhydryl]-5-dimethylaminobenzoic acid from part A above was oxidized to obtain 2.38 g of 3-dimethylaminophenyl-3-methylaminophenyl-6-dimethylaminophthalide (Formula I: $R=CH_3$; $X=H$; $Y=4-(CH_3)_2NC_6H_4$; $Z=4-CH_3NHC_6H_4$) as a tan-colored solid melting over the range 126°-135° C.

The infrared spectral analysis showed a maximum at 1751 ($C=O$; s) cm$^{-1}$. The nuclear magnetic resonance spectrum was concordant with the assigned structure.

A toluene solution of the product spotted on silica gel, an acidic clay or a phenolic resin develops a reddish-blue-colored image.

EXAMPLE 29

A. Employing a procedure similar to that described in Example 26, part A above, 5.4 g of 3-(4-dimethylaminophenyl)-5-dimethylaminophthalide, prepared as described in Example 1, part A above and 57 g of N,N-diethyl-m-toluidine were interacted in the presence of anhydrous zinc chloride at 100° to 110° C. to obtain 4.5 g of 2-[(2-methyl-4-diethylamino-4'-dimethylamino)benzhydryl]-5-dimethylaminobenzoic acid (Formula III: $R=CH_3$; $X=H$; $Y=4-(CH_3)_2NC_6H_4$; $Z=2-CH_3-4-(C_2H_5)NC_6H_4$) as a brownish-pink colored solid which melted over the range 105°-115° C.

A significant infrared maximum appeared at 1700 ($C=O$; s) cm$^{-1}$. The nuclear magnetic resonance spectrum was in accord with the assigned structure.

B. Proceeding in a manner similar to that described in Example 27, part B above, 3.7 g of 2-[(2-methyl-4-diethylamino-4'-dimethylamino)benzhydryl]-5-dimethylaminobenzoic acid from part A above was oxidized to obtain 1.8 g of 3-(2-methyl-4-diethylaminophenyl)-3-(4-dimethylaminophenyl)-6-dimethylaminophthalide (Formula I: $R=CH_3$; $X=H$; $Y=4-(CH_3)_2NC_6H_4$; $Z=2-CH_3-4-(C_2H_5)_2NC_6H_3$) as a brown solid which melted at 190°-195° C.

A significant infrared maximum appeared at 1760 ($C=O$; s) cm$^{-1}$. The nuclear magnetic resonance spectrum was in accord with the assigned structure.

A toluene solution of the product when spotted on silica gel or a phenolic resin develops a purple-colored image.

EXAMPLE 30

A. Following a procedure similar to that described above in Example 1, part A, 36.6 g of 2-chloro-4-dimethylaminobenzaldehyde and 33.0 g of 4-dimethylaminobenzoic acid were interacted in acetic anhydride to obtain 52.1 g of 3-(2-chloro-4-dimethylaminophenyl)-6-dimethylaminophthalide (Formula I: $R=CH_3$; $X=Z=H$; $Y=2-Cl-4-(CH_3)_2NC_6H_3$) as a red crystalline solid which melted at 159°-160° C.

A significant infrared maximum appeared at 1770 ($C=O$; s) cm$^{-1}$.

B. Employing a procedure similar to that described in Example 26, part A above, 6.5 g of 3-(2-chloro-4-dimethylaminophenyl)-6-dimethylphthalide from part A above and 30.0 ml of N,N-dimethylaniline were interacted in the presence of 5.3 g of anhydrous zinc chloride to obtain 8.0 g of 2-[2-chloro-4,4'-dimethylamino)benzhydryl]-5-dimethylaminobenzoic acid (Formula III: $R=CH_3$; $X=H$; $Y=2-Cl-4-(CH_3)_2NC_6H_3$; $Z=4-(CH_3)_2NC_6H_4$) as a pink powder which melted over the range 180°-190° C.

The infrared spectrum showed a maximum at 1610 ($C=O$; s, b) cm$^{-1}$. The nuclear magnetic resonance was concordant with the assigned structure.

C. Proceeding in a manner similar to that described in Example 27, part B above, 5.4 g of 2-[2-chloro-4,4'-bis(- dimethylamino)benzhydryl]-5-dimethylaminobenzoic acid was oxidized to obtain 2.9 g of 3-(2-chloro-4-dimethylaminophenyl)-3-(4-dimethylaminophenyl)-6-dimethylaminophthalide (Formula I: R=CH$_3$; X=H; Y=2-Cl-4-(CH$_3$)$_2$NC$_6$H$_3$; Z=4-(CH$_3$)$_2$NC$_6$H$_4$), a pale bluish-gray-colored solid which melted at 233°–234° C.

A significant infrared maximum appeared at 1760 (C=O; s) cm$^{-1}$. The nuclear magnetic resonance spectrum was concordant with the assigned structure.

A toluene solution of the product spotted on silica gel develops a bluish-purple-colored image.

EXAMPLE 31

A. Employing a procedure similar to that described in Example 26, part A above, 7.0 g of 3-(2,4-dimethoxyphenyl)-6-dimethylaminophthalide, prepared as described in Example 18, part A above and 31.0 ml of N,N-dimethylaniline were interacted in the presence of zinc chloride at room temperature to obtain 10.9 g of 2-(2,4-dimethoxy-4'-dimethylaminobenzhydryl)-5-dimethylaminobenzoic acid (Formula III: R=CH$_3$; X=H; Y=2,4-(CH$_3$O)$_2$C$_6$H$_3$; Z=4-(CH$_3$)$_2$NC$_6$H$_4$), a white solid which melted over the range 105°–135° C.

The infrared spectrum had a significant maximum at 1696 (C=O; s) cm$^{-1}$. The nuclear magnetic resonance spectrum was consistent with the assigned structure.

B. Following a procedure similar to that described in Example 27, part B above, 6.5 g of 2-(2,4-dimethoxy-4'-dimethylaminobenzhydryl)-5-dimethylaminobenzoic acid was oxidized to obtain 2.2 g of 3-(2,4-dimethoxyphenyl)-3-(4-dimethylaminophenyl)-6-dimethylaminophthalide (Formula I: R=CH$_3$; X=H; Y=2,4-(CH$_3$O)$_2$—C$_6$H$_3$; Z=4-(CH$_3$)$_2$NC$_6$H$_4$), a pale yellow-colored solid which melted at 191.5°–193.5° C.

A significant infrared maximum appeared at 1758 (C=O; s) cm$^{-1}$. The nuclear magnetic resonance spectrum was in accord with the assigned structure.

A toluene solution of the product spotted on a phenolic resin develops a light blue-colored image.

EXAMPLE 32

A. Proceeding in a manner similar to that described in Example 26, part A above, 9.9 g of 3-(2-methoxyphenyl)-6-dimethylaminophthalide, prepared as described in Example 13, part A above and 49.0 ml of N,N-dimethylaniline were interacted in the presence of zinc chloride at room temperature to obtain 14.3 g of 2-(2-methoxy-4'-dimethylaminobenzhydryl)-5-dimethylaminobenzoic acid (Formula III: R=CH$_3$; X=H; Y=2-CH$_3$OC$_6$H$_4$; Z=4-(CH$_3$)$_2$NC$_6$H$_4$), a light yellow solid which melted over the range 229°–234° C.

The infrared spectrum had a significant maximum at 1690 (C=O; s) cm$^{-1}$. The nuclear magnetic resonance spectrum was consistent with the assigned structure.

B. Employing a procedure similar to that described in Example 27, part B above, 6.1 g of 2-(2-methoxy-4'-dimethylaminobenzhydryl)-5-dimethylaminobenzoic acid was oxidized with hydrogen peroxide to obtain 1.05 g of 3-(2-methoxyphenyl)-3-(4-dimethylaminophenyl)-6-dimethylaminophthalide (Formula I: R=CH$_3$; X=H; Y=2-CH$_3$OC$_6$H$_4$; Z=4-(CH$_3$)$_2$NC$_6$H$_4$), a light yellow-colored solid which melted at 215°–216° C.

A significant infrared maximum appeared at 1750 (C=O; s) cm$^{-1}$. The nuclear magnetic resonance spectrum was consistent with the assigned structure.

A toluene solution of the product spotted on silica gel develops a light blue-colored image and spotted on a phenolic resin develops a light green-colored image.

EXAMPLE 33

A. Following the procedure described above in Example 26, part A, 14.2 g of 3-(4-methoxyphenyl)-6-dimethylaminophthalide prepared as described in Example 12, part A above and 35.0 ml of 1-ethyl-2-methylindole were interacted in the presence of anhydrous zinc chloride at a temperature in the range of 90° to 110° C. to obtain 15.5 g of 2-[α-(4-methoxyphenyl)-α-(1-ethyl-2-methyl-3-indolyl)]methyl-5-dimethylaminobenzoic acid (Formula III: R=CH$_3$; X=H; Y=4-CH$_3$OC$_6$H$_4$; Z=4-(CH$_3$)$_2$NC$_6$H$_4$), a light gray-colored solid which melted over the range 115°–126° C.

The infrared spectrum had a significant maximum at 1683 (C=O; s) cm$^{-1}$. The nuclear magnetic resonance spectrum was consistent with the assigned structure.

B. Proceeding in a manner similar to that described in Example 1, part C above, 2-[α-(4-methoxyphenyl)-α-(1-ethyl-2-methyl-3-indolyl)]methyl-5-dimethylaminobenzoic acid is oxidized to obtain 3-(4-methoxyphenyl)-3-(1-ethyl-2-methyl-3-indolyl)-6-dimethylaminophthalide (Formula I: R=CH$_3$; X=H; Y=4-CH$_3$OC$_6$H$_4$; Z=4-(CH$_3$)$_2$NC$_4$H$_4$).

EXAMPLE 34

A. Employing a procedure similar to that described in Example 1, part A above, 13.3 g of 2-butoxy-4-diethylaminobenzaldehyde and 9.7 g of m-dimethylaminobenzoic acid were refluxed in acetic anhydride to obtain 3-(2-butoxy-4-diethylaminophenyl)-6-dimethylaminophthalide (Formula I: R=CH$_3$; X=Z=H; Y=2-C$_4$H$_9$O-4-(C$_2$H$_5$)$_2$NC$_6$H$_3$) as a tarry residue.

The infrared spectrum had a significant maximum which appeared at 1760 (C=O; s) cm$^{-1}$. The nuclear magnetic resonance spectrum was in accord with the assigned structure.

B. Proceeding in a manner similar to Example 26, part A above, 3-(2-butoxy-4-diethylaminophenyl)-6-dimethylaminophthalide from part A above is interacted with 1-octyl-2-ethylindole to obtain 2-[α-(2-butoxy-4-diethylaminophenyl)-α-(1-octyl-2-ethyl-3-indolyl)]methyl-5-dimethylaminobenzoic acid (Formula III: R=CH$_3$; X=H; Y=2-C$_4$H$_9$O-4-(C$_2$H$_5$)$_2$NC$_6$H$_3$; Z=1-C$_8$H$_{17}$-2-C$_2$H$_5$-3-indolyl).

C. Following the procedure described in Example 2, part B above, 2-[α-(2-butoxy-4-diethylaminophenyl)-α-(1-octyl-2-ethyl-3-indolyl)]methyl-5-dimethylaminobenzoic acid from B above is oxidized to obtain 3-(2-butoxy-4-diethylaminophenyl)-3-(1-octyl-2-ethyl-3-indolyl)-6-dimethylaminophthalide (Formula I: R=CH$_3$; X=H; Y=2-C$_4$H$_9$O-4-(C$_2$H$_5$)$_2$NC$_6$H$_3$; Z=1-C$_8$H$_{17}$-2-C$_2$H$_5$-3-indolyl).

EXAMPLE 35

A. Proceeding in a manner similar to that described in Example 5, part A above, 7.4 g of 3-(4-dimethylaminophenyl)-6-dimethylaminophthalide, prepared as described in Example 1, part A above and 3.0 g of N,N-dimethylaniline were interacted in 40 g of ethylene dichloride in the presence of 6.65 g of anhydrous aluminum chloride at reflux to obtain 2.7 g of 2-[4,4'-bis(dimethylamino)benzhydryl]-5-dimethylaminobenzoic acid (Formula III: R=CH$_3$; X=H; Y=Z=4-(CH$_3$)$_2$NC$_6$H$_4$), a pale blue solid.

A significant infrared maximum appeared at 1700 (C—O; s, b) cm$^{-1}$. The nuclear magnetic resonance spectrum was consistent with the assigned structure.

B. Following the procedure similar to that described in Example 1, part C above, 2-[4,4'-bis(dimethylamino)-benzhydryl]-5-dimethylaminobenzoic acid is oxidized to obtain 3,3-bis(4-dimethylaminophenyl)-6-dimethylaminophthalide (Formula I: R=CH$_3$; X=H; Y=Z=4-(CH$_3$)$_2$NC$_6$H$_4$).

It is contemplated that by following the procedure described in Example 1, part A, but using in place of p-dimethylaminobenzaldehyde and m-dimethylaminobenzoic acid approximately molar equivalent quantities of the appropriate Y-CHO and 3-N(R)$_2$-4-X-benzoic acid the compounds of Examples 36–50 are obtained.

EXAMPLE 36

3-(2-Methylphenyl)-6-[N-methyl-N-(4-methylbenzyl)]aminophthalide using 2-methylbenzaldehyde and 3-[N-methyl-N-(4-methylbenzyl)amino]benzoic acid.

EXAMPLE 37

3-(1-Ethyl-2-phenyl-3-indolyl)-5-iodo-6-diethylaminophthalide using 1-ethyl-2-phenylindole-3-carboxaldehyde and 3-diethylamino-4-iodobenzoic acid.

EXAMPLE 38

3-(4-Pyridinyl)-6-dibenzylaminophthalide using 4-pyridinecarboxaldehyde and 3-dibenzylaminobenzoic acid.

EXAMPLE 39

3-(2,3-Dimethoxyphenyl)-6-diethylaminophthalide using 2,3-dimethoxybenzaldehyde and 3-diethylaminobenzoic acid.

EXAMPLE 40

3-(2-Methyl-1-n-octyl-3-indolyl)-5-chloro-6-aminophthalide using 2-methyl-1-n-octylindole-3-carboxaldehyde and 3-amino-4-chlorobenzoic acid.

EXAMPLE 41

3-(5-Methoxy-3-indolyl)-6-(N-ethylbenzylamino)phthalide using 5-methoxyindole-3-carboxaldehyde and 3-(N-ethylbenzylamino)benzoic acid.

EXAMPLE 42

3-(2,3,4-Trimethoxyphenyl)-6-(N-ethyl-N-butylamino)phthalide using 2,3,4-trimethoxybenzaldehyde and 3-(N-ethyl-N-butylamino)benzoic acid.

EXAMPLE 43

3-(2-Pyridinyl)-5-chloro-6-dimethylaminophthalide using 2-pyridinecarboxyaldehyde and 3-dimethylamino-4-chlorobenzoic acid.

EXAMPLE 44

3-(2-Bromophenyl)-6-[N-methyl-N-(4-chlorobenzyl)amino]phthalide using 2-bromobenzaldehyde and 3-[N-methyl-N-(4-chlorobenzyl)amino]benzoic acid.

EXAMPLE 45

3-[2-Methyl-4-(N-methylbenzylamino)phenyl]-5-bromo-6-ethylaminophthalide using 2-methyl-4-(N-methylbenzylamino)benzaldehyde and 3-ethylamino-4-bromobenzoic acid.

EXAMPLE 46

3-(2-Fluorophenyl)-6-(N-ethyl-N-methylamino)phthalide using 2-fluorobenzaldehyde and 3-(N-ethyl-N-methylamino)benzoic acid.

EXAMPLE 47

3-(2-Pyrrolyl)-5-fluoro-6-propylaminophthalide using 4-pyrrole-2-carboxaldehyde and 3-propylamino-4-fluorobenzoic acid.

EXAMPLE 48

3-(1-n-Butyl-2-phenyl-3-indolyl)-6-ethylaminophthalide using 1-n-butyl-2-phenylindole-3-carboxaldehyde and 3-ethylaminobenzoic acid.

EXAMPLE 49

3-(2-Methoxy-4-diethylaminophenyl)-6-methylaminophthalide using 2-methoxy-4-diethylaminobenzaldehyde and 3-methylaminobenzoic acid.

EXAMPLE 50

3-(3-Ethoxyphenyl)-6-aminophthalide using 3-ethoxybenzaldehyde and 3-aminobenzoic acid.

It is contemplated that by following a procedure selected from those described in Example 1, part B, Example 2, part B, Example 5, part A, or Example 26, part A for interacting approximately molar equivalent quantities of the appropriate 3-Y-5-X-6-N(R)$_2$phthalide and Z—H in the presence of the indicated condensing agent, the compounds of Examples 51–65 are obtained.

EXAMPLE 51

2-[β-(3-Isopropyl-4-diethylamino-2'-methyl)benzhydryl]-5-[N-methyl-N-(4-methylbenzyl)amino]benzoic acid using 3-(2-methylphenyl)-6-[N-methyl-N-(4-methylbenzyl)aminophthalide and N,N-diethyl-3-isopropylaniline in the presence of oxalic acid after Example 2, part B.

EXAMPLE 52

2-{α-(1-Ethyl-2-phenyl-3-indolyl)-α-[4-(N-isobutyl-N-ethylamino)phenyl]}methyl-4-iodo-5-diethylaminobenzoic acid using 3-(1-ethyl-2-phenyl-3-indolyl)-5-iodo-6-diethylaminophthalide and N-isobutyl-N-ethylaniline in the presence of lithium carbonate after Example 1, part A.

EXAMPLE 53

2-[α-(4-Pyridinyl)-α-(4-diethylamino-2-propoxyphenyl)]-methyl-5-dibenzylaminobenzoic acid using 3-(4-pyridinyl)-6-dibenzylaminophthalide and N,N-diethyl-2-propoxyaniline in the presence of phosphorous trichloride after Example 26, part A.

EXAMPLE 54

2-{α-[1-(4-Bromobenzyl)-2-isopropyl-3-indolyl]-α-(2,3-dimethoxyphenyl)}methyl-5-diethylaminobenzoicacid using 3-(2,3-dimethoxyphenyl)-6-diethylaminophthalide and 1-(4-bromobenzyl)-2-isopropylindole in the presence of methanesulfonic acid after Example 2, part A.

EXAMPLE 55

2-[α-(2-Methyl-1-n-octyl-3-indolyl)-α-(N-isopropyl-3-pyrrolyl)]methyl-4-chloro-5-aminobenzoic acid using 3-(2-methyl-1-n-octyl-3-indolyl)-5-chloro-6-aminophthalide and N-isopropylpyrrole in the presence of diethanolmethylamine after Example 1, part B.

EXAMPLE 56

2-{α-[(2-Ethoxy-4-diethylamino)phenyl]-α-(5-methoxy-3-indolyl)}methyl-5-(N-ethylbenzylamino)benzoic acid using 3-(5-methoxy-3-indolyl)-6-(N-ethylbenzylamino)phthalide and N,N-diethyl-2-ethoxyaniline in the presence of lithium hydroxide after Example 1, part B.

EXAMPLE 57

2-[α-(2,3,4-Trimethoxyphenyl)-α-(1-isoamyl-3-indolyl)]methyl-5-(N-ethyl-N-butylamino)benzoic acid using 2-(2,3,4-trimethoxyphenyl)-6-(N-ethyl-N-butylamino)phthalide and 1-isoamylindole in the presence of triethanolamine after Example 1, part B.

EXAMPLE 58

2-[α-(2-Methoxy-3-chloro-4-diethylaminophenyl)-α-(2-pyridinyl)]methyl-4-chloro-5-dimethylaminobenzoic acid using 3-(2-pyridinyl)-5-chloro-6-dimethylaminophthalide and N,N-diethyl-2-methoxy-3-chloroaniline in the presence of citric acid after Example 2, part A.

EXAMPLE 59

2-[2-Bromo-2',4'-bis-(diisopropylamino)]benzhydryl-5-[N-methyl-N-(4-chlorobenzyl)amino]benzoic acid using 3-(2-bromophenyl)-6-[N-methyl-N-(4-chlorobenzyl)amino]phthalide and N,N,N',N'-tetraisopropyl-m-phenylenediamine in the presence of 1,4-diazabicyclo[2,2,2]octane after Example 1, part B.

EXAMPLE 60

2-[(2-Methyl-2-fluoro-4-N-methylbenzylamino-4'-dibutylamino)benzhydryl]-4-bromo-5-ethylaminobenzoic acid using 3-[2-methyl-4-(N-methylbenzylamino)phenyl]-5-bromo-6-ethylaminophthalide and N,N-dibutyl-3-fluoroaniline in the presence of phosphoric acid after Example 2, part A.

EXAMPLE 61

2-[(2'-Fluoro-3-propoxy-4-N-sec-butylbenzylamino)benzhydryl]-5-(N-ethyl-N-methylamino)benzoic acid using 3-(2-fluorophenyl)-6-(N-ethyl-N-methyl)aminophthalide and N-benzyl-N-sec-butyl-2-propoxyaniline in the presence of boron trifluoride after Example 26, part A.

EXAMPLE 62

2-[α-(3-Indolyl)-α-(2-phenyl-5,6-dichloro-3-indolyl)]methyl-4-fluoro-5-(N-propyl)aminobenzoic acid using 3-(3-indolyl)-5-fluoro-6-propylaminophthalide and 5,6-dichloro-2-phenylindole in the presence of glycolic acid after Example 2, part A.

EXAMPLE 63

2-[α-(2-Iodo-4-N-n-butylbenzylaminophenyl)-α-(1-n-butyl-2-phenyl-3-indolyl)]methyl-5-N-ethylaminobenzoic acid using 3-(1-n-butyl-2-phenyl-3-indolyl)-6-ethylaminophthalide and N-benzyl-N-butyl-3-iodoaniline in the presence of hydrochloric acid after Example 2, part A.

EXAMPLE 64

2-[α-(2-Methoxy-4-diethylaminophenyl)-α-(1-methyl-6-nitro-3-indolyl)]methyl-5-N-methylaminobenzoic acid using 3-(2-methoxy-4-diethylaminophenyl)-6-methylaminophthalide and 1-methyl-6-nitroindole in the presence of toluenesulfonic acid after Example 2, part A.

EXAMPLE 65

2-[α-(3-Butoxyphenyl)-α-(2-isopropyl-3-indolyl)-]methyl-5-aminobenzoic acid using 3-(3-butoxyphenyl)-6-aminophthalide and 2-isopropylindole in the presence of phosphorus oxychloride after Example 2, part B.

It is contemplated that by following an oxidation procedure selected from those described in Example 1, part C, Example 2, part B, Example 3, part B or Example 27, part B, for oxidizing the appropriate 2-(α-Y-α-Z)methyl-4-X-5-N(R)₂-benzoic acid the compounds of Examples 66–80 are obtained.

EXAMPLE 66

3-(2-Methylphenyl)-3-(3-isopropyl-4-diethylaminophenyl)-6-[N-methyl-N-(4-methylbenzyl)]aminophthalide using 2-[(3-isopropyl-4-diethylamino-2'-methyl)benzhydryl]-5-[N-methyl-N-(4-methylbenzyl)amino]benzoic acid.

EXAMPLE 67

3-(1-Ethyl-2-phenyl-3-indolyl)-3-[4-(N-isobutyl-N-ethylamino)phenyl]-5-iodo-6-diethylaminophthalide using 2-{α-(1-ethyl-2-phenyl-3-indolyl)-α-[4-(N-isobutyl-N-ethylamino)phenyl]}methyl-4-iodo-5-diethylaminobenzoic acid.

EXAMPLE 68

3-(4-Pyridinyl)-3-(4-diethylamino-2-propoxyphenyl)-6-dibenzylaminophthalide using 2-[α-(4-pyridinyl)-α-(4-diethylamino-2-propoxyphenyl)]methyl-5-dibenzylaminobenzoic acid.

EXAMPLE 69

3-[1-(4-Bromobenzyl)-2-isopropyl-3-indolyl]-3-(2,3-dimethoxyphenyl)-6-diethylaminophthalide using 2-{α-[1-(4-bromobenzyl)-2-isopropyl-3-indolyl]-α-(2,3-dimethoxyphenyl)}methyl-5-diethylaminobenzoic acid.

EXAMPLE 70

3-(2-Methyl-1-n-octyl-3-indolyl)-3-(N-isopropyl-3-pyrrolyl)-5-chloro-6-aminophthalide using 2-[α-(2-methyl-1-n-octyl-3-indolyl)-α-(N-isopropyl-3-pyrrolyl)]methyl-4-chloro-5-aminobenzoic acid.

EXAMPLE 71

3-(2-Ethoxy-4-diethylaminophenyl)-3-(5-methoxy-3-indolyl)-6-(N-ethylbenzylamino)phthalide using 2-{α-[(2-ethoxy-4-diethylamino)phenyl]-α-(5-methoxy-3-indolyl)}methyl-5-(N-ethylbenzylamino)benzoic acid.

EXAMPLE 72

3-(2,3,4-Trimethoxyphenyl)-3-(1-isoamyl-3-indolyl)-5-(N-ethyl-N-butylamino)phthalide using 2-[α-(2,3,4-trimethoxyphenyl)-α-(1-isoamyl-3-indolyl)]methyl-5-(N-ethyl-N-butylamino)benzoic acid.

EXAMPLE 73

3-(2-Methoxy-3-chloro-4-diethylaminophenyl)-3-(2-pyridinyl)-5-chloro-6-dimethylaminophthalide using 2-[α-(2-methoxy-3-chloro-4-diethylaminophenyl)-α-(2-pyridinyl)]methyl-4-chloro-5-dimethylaminobenzoic acid.

EXAMPLE 74

3-(2-Bromophenyl)-3-[2,4-bis(diisopropylamino)-phenyl]-6-[N-methyl-N-(4-chlorobenzyl)amino]phthalide using 2-{[2-bromo-2',4'-bis(diisopropylamino)]-benzhydryl}-5-[N-methyl-N-(4-chlorobenzyl)amino]benzoic acid.

EXAMPLE 75

3-(2-Methyl-4-N-methylbenzylaminophenyl)-3-(2-fluoro-4-dibutylaminophenyl)-5-bromo-6-ethylaminophthalide using 2-[(2-methyl-2'-fluoro-4-N-methylbenzylamino-4'-dibutylamino)benzhydryl]-4-bromo-5-ethylaminobenzoic acid.

EXAMPLE 76

3-(2-Fluorophenyl)-3-[3-propoxy-4(N-sec-butylbenzylamino)phenyl]-6-(N-ethyl-N-methyl)aminophthalide using 2-[(2'-fluoro-3-propoxy-4-N-sec-butylbenzylamino)benzhydryl]-5-(N-ethyl-N-methyl)aminobenzoic acid.

EXAMPLE 77

3-(3-Indolyl)-3-(2-phenyl-5,6-dichloro-3-indolyl)-5-fluoro-6-(N-propyl)aminophthalide using 2-[α-(3-indolyl)-α-(2-phenyl-5,6-dichloro-3-indolyl)]methyl-4-fluoro-5-(N-propyl)aminobenzoic acid.

EXAMPLE 78

3-[2-Iodo-4-(N-n-butylbenzylamino)phenyl]-3-(1-n-butyl-2-phenyl-3-indolyl)-6-N-ethylaminophthalide using 2-{α-[2-iodo-4-(N-n-butylbenzylamino)phenyl]-α-(1-n-butyl-2-phenyl-3-indolyl)}methyl-5-N-ethylaminobenzoic acid.

EXAMPLE 79

3-(2-Methoxy-4-diethylaminophenyl)-3-(1-methyl-6-nitro-3-indolyl)-5-N-methylaminophthalide using 2-[α-(2-methoxy-4-diethylaminophenyl)-α-(1-methyl-6-nitro-3-indolyl)]methyl-5-N-methylaminobenzoic acid.

EXAMPLE 80

3-(3-Butoxyphenyl)-3-(2-isopropyl-3-indolyl)-6-aminophthalide using 2-[α-(3-butoxyphenyl)-α-2-isopropyl-3-indolyl)]methyl-5-aminobenzoic acid.

EXAMPLE 81

The use of the compounds of Formulas I through III and described in Examples 1 through 80 as color forming components in pressure-sensitive microencapsulated copying systems is illustrated with reference to the product of Example 1, part C.

A. A mixture of 196 ml of distilled water and 15.0 g of pigskin gelatin was stirred at approximately 50° C. for approximately 45 minutes. There was then added to the mixture a warmed (approximately 50° C.) solution of 49.0 g of alkylated biphenyls and 1.0 g of 3-[2,4-bis(-dimethylamino)phenyl]-3-(4-dimethylaminophenyl)-6-dimethylaminophthalide (Formula I: $R=CH_3$; $X=H$; $Y=4-(CH_3)_2NC_6H_4$; $Z=2,4-[(CH_3)_2N]_2C_6H_3$), prepared as described above in Example 1, part C. The resulting solution was stirred for approximately fifteen minutes. A second solution of 81.0 ml of distilled water and 10.0 g of gum arabic was then prepared and warmed to approximately 50° C. for approximately one hour.

B. The two solutions, the first containing water, gelatin, alkylated biphenyls and the product, and the second containing water and gum arabic were mixed and the pH adjusted to 9 by the addition of approximately 0.7 ml of 20 percent aqueous sodium hydroxide. The resulting mixture was transferred to a larger reactor equipped with a variable speed one-half horse power Eppenbach Homo-Mixer (Gifford-Wood Co., Hudson, N.Y.) and there was added over a period of two to three minutes 650 ml of distilled water which had been heated to 50° C. With the stirrer running at an applied voltage of between 20 to 25 volts, there was slowly added sufficient ten percent aqueous acetic acid to set the pH at 4.5, this being the point where coacervation was initiated. The stirrer speed was increased by raising the applied voltage to approximately thirty volts and approximately four drops of 2-ethylhexanol were added to suppress foaming. After approximately twenty minutes, a sample of the suspension was examined microscopically and found to have stabilized in the range of 20 to 25 microns particle size whereupon an external ice/water bath was immediately placed around the reactor containing the suspension. At approximately 20° C., the agitation speed was reduced by decreasing the applied voltage to the range of 20 to 25 volts. Cooling was continued and at approximately 15° C., 10.0 ml of glutaraldehyde was added over a period of five minutes. When the internal temperature reached 10° C., the agitation speed was further reduced by lowering the applied voltage to approximately 20 volts and these conditions maintained for approximately thirty minutes. At this time, the Eppenbach Homo-Mixer was replaced with a conventional blade type laboratory agitator and the suspension was stirred an additional three hours during which period the temperature was allowed to warm to room temperature. The microencapsulated product was isolated by pouring the slurry through an ASTM #18 stainless steel sieve to remove any large agglomerates and then collecting the capsules by filtration. The collected capsules were washed successively with four 100 ml portions of distilled water each and stored as a water-wet pulp. A sample of the pulp analyzed by drying in vacuo at 80° C. was found to consist of 37.5 percent solids.

C. To 125 ml of distilled water, 10.6 g of oxidized corn starch was added over a period of ten to fifteen minutes with stirring. This mixture was heated to a temperature in the range of 70°–80° C. and maintained until all the starch dissolved. The starch solution was cooled to ambient temperature and there was added 100 g of the capsule-containing water-wet pulp from part B above and 43.0 ml of distilled water. The capsules and starch solution were mixed at room temperature using an Eppenbach Homo-Mixer set at an applied voltage of 25 volts for five minutes and then at an applied voltage of 30 volts for an additional five minutes to complete the suspension of the capsules in the starch solution.

D. The stock starch-microcapsule suspension prepared in part C above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep blue-colored image promptly formed.

When evaluated in a duplicating system prepared and tested as described above, the product of Example 6, part B, 3-(2-ethoxy-4-diethylaminophenyl)-3-(4-dimethylaminophenyl)-6-dimethylphthalide (Formula I: $R=CH_3$; $X=H$; $Y=2-C_2H_5O-4-(C_2H_5)_2NC_6H_3$; $Z=4-(CH_3)_2NC_6H_4$), produced a blue-colored developed image; the product of Example 10, part D, 3-[4-(N-ethylbenzylamino)phenyl]-3-(1-ethyl-2-methyl-3-indolyl)-6-dimethylaminophthalide (Formula I: $R=CH_3$; $X=H$; $Y=4-(C_6H_5CH_2)(C_2H_5)NC_6H_4$; $Z=1-C_2H_5-2-CH_3-3$-indolyl), produced a purple-colored developed image; the product of Example 24, part A, 3-(1-ethyl-2-methyl-3-indolyl)-6-dimethylaminophthalide (Formula II: $R=CH_3$; $X=H$; $Y=1-C_2H_5-2-CH_3-3$-indolyl), produced a light-red-colored developed image; the product of Example 10, part A, 3-[4-(N-ethylbenzylamino)phenyl]-6-dimethylaminophthalide (Formula II: $R=CH_3$; $X=H$; $Y=4-(C_6H_5CH_2)(C_2H_5)NC_6H_4$), produced a green-colored developed image; the produce of Example 8, part A, 3-(4-diethylaminophenyl)-6-dimethylaminophthalide (Formula II: $R=CH_3$; $X=H$; $Y=4-(C_2H_5)_2NC_6H_4$), produced a green-colored developed image; the product of Example 2, part A, 2-[α-(1-ethyl-2-methyl-3-indolyl)-α-(4-dimethylaminophenyl)]methyl-5-dimethylaminobenzoic acid (Formula III: $R=CH_3$; $X=H$; $Y=4-(CH_3)_2NC_6H_4$; $Z=1-C_2H_5-2-CH_3-3$-indolyl), produced a purple-colored developed image; the product of Example 1, part B, 2-[2,4,4'-tris(dimethylamino)benzhydryl]-5-dimethylaminobenzoic acid (Formula III: $R=CH_3$; $X=H$; $Y=4-(CH_3)_2NC_6H_4$; $Z=2,4-[(CH_3)_2N]_2C_6H_3$), produced a bluish-purple-colored developed image.

EXAMPLE 82

The utility of the compounds of Formulas I through III whose preparations are described in the foregoing examples as color forming components in thermal marking systems is illustrated by the incorporation and testing of the compound of Example 1, part C, 3-[2,4-bis(dimethylamino)phenyl]-3-(4-dimethylaminophenyl)-6-dimethylaminophthalide (Formula I: $R=CH_3$; $X=H$; $Y=4-(CH_3)_2NC_6H_4$; $Z=2,4-[(CH_3)_2N]_2C_6H_3$) in a thermal sensitive marking paper. The test paper was prepared by a procedure similar to that described in U.S. Pat. No. 3,539,375.

A. A mixture of 2.0 g of 3-[2,4-bis(dimethylamino)phenyl]-3-(4-dimethylaminophenyl)-6-dimethylaminophthalide, 8.6 g of a ten percent aqueous solution of polyvinyl alcohol (approximately 99 percent hydrolyzed), 3.7 g of water and 31.6 g of 1/16 inch diameter zirconium grinding beads which was charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from A and 47.9 g of the slurry from B. The mixture was then uniformly coated on sheets of paper at thicknesses of approximately 0.003 inch and the coated sheets airdried. The coated paper was tested by tracing a design on the coated side of the paper placed on a smooth flat surface with a stylus heated to approximately 130° C. A deep purple-colored image corresponding to the traced design promptly developed.

When evaluated in a thermal marking system by heating in admixture with Bisphenol A, the product of Example 6, part B, 3-(2-ethoxy-4-diethylaminophenyl)-3-(4-dimethylaminophenyl)-6-dimethylphthalide (Formula I: $R=CH_3$; $X=H$; $Y32 2-C_2H_5O-4-(C_2H_5)_2NC_6H_3$; $Z=4-(CH_3)_2NC_6H_4$), produced a blue-colored developed image; the product of Example 10, part D, 3-[4-(N-ethylbenzylamino)phenyl]-3-(1-ethyl-2-methyl-3-indolyl)-6-dimethylaminophthalide (Formula I: $R=CH_3$; $X=H$; $Y=4-(C_6H_5CH_2)(C_2H_5)NC_6H_4$; $Z=1-C_2H_5-2-CH_3-3$-indolyl), produced a dark blue-colored developed image; the product of Example 24, part A, 3-(1-ethyl-2-methyl-3-indolyl)-6-dimethylaminophthalide (Formula II: $R=CH_3$; $X=H$; $Y=1-C_2H_5-2-CH_3-3$-indolyl), produced a purple-colored developed image; the product of Example 10, part A, 3-[4-(N-ethylbenzylamino)phenyl]-6-dimethylaminophthalide (Formula II: $R=CH_3$; $X=H$; $Y=4-(C_6H_5CH_2)(C_2H_5)NC_6H_4$), produced a green-colored developed image; the product of Example 12, part A, 3-(4-methoxyphenyl)-6-dimethylaminophthalide (Formula II: $R=CH_3$; $X=H$; $Y=4-CH_3OC_6H_4$), produced a yellow-colored developed image; the product of Example 14, part A, 3-(4-ethoxyphenyl)-6-dimethylaminophthalide (Formula II: $R=CH_3$; $X=H$; $Y=4-C_2H_5OC_6H_4$), produced a yellow-colored developed image; the product of Example 21, part A, 3-[1-(3,4-methylenedioxy)phenyl]-6-dimethylaminophthalide (Formula II: $R=CH_3$; $X=H$; $Y=1-(3,4-OCH_2OC_6H_3)$, produced a yellowish-brown-colored developed image; the product of Example 1, part B, 2-(2,4,4'-tris(dimethylamino)benzhydryl]-5-dimethylaminobenzoic acid (Formula III: $R=CH_3$; $X=H$; $Y=4-(CH_3)_2NC_6H_4$; $Z=2,4-[(CH_3)_2N]_2C_6H_3$), produced a blue-colored developed image; the product of Example 2, part A, 2-[α-(4-dimethylaminophenyl)-α-(1-ethyl-2-methyl-3-indolyl)-methyl-5-dimethylaminobenzoic acid (Formula III: $R=CH_3$; $X=H$; $Y=4-(CH_3)_2NC_6H_4$; $Z=1-C_2H_5-2-CH_3-3$-indolyl), produced a purple-colored developed image.

We claim:

1. A 3-(2-$R^{3'}$-4-$R^{1'}$-phenyl)-3-(2-$R^3$-3-$R^{2'}$-4-$R^{1''}$-phenyl) 5-X-6-N(R)$_2$phthalide of the formula

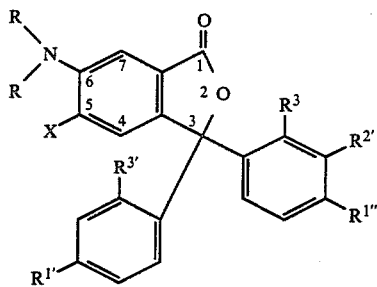

wherein:

R represents non-tertiary alkyl of one to four carbon atoms;

$R^{1'}$ represent non-tertiary alkoxy of one to three carbon atoms;

$R^{1''}$ represent dialkylamino in which alkyl is non-tertiary alkly of one to four carbon atoms;

$R^{2'}$ represents hydrogen or alkyl of one to three carbon atoms;

$R^3$ represents hydrogen, alkyl of one to three carbon atoms, non-tertiary alkoxy of one to four carbon atoms, halo or dialkylamino in which alkyl is non-tertiary alkyl of one to four carbon atoms;

$R^{3'}$ represents hydrogen, alkyl of one to three carbon atoms, non-tertiary alkoxy of one to four carbon atoms or halo; and X represents hydrogen or halo.

2. 3-(4-Dimethylaminophenyl)-3-(4-methoxyphenyl)-6-dimethylaminophthalide according to claim 1.

3. 3-[2,4-Bis(dimethylamino)phenyl]-3-(4-methoxyphenyl)-6-dimethylaminophthalide according to claim 1.

* * * * *